(12) United States Patent
Yamaguchi et al.

(10) Patent No.: US 8,909,495 B2
(45) Date of Patent: Dec. 9, 2014

(54) PARTICLE RADIATION MONITORING APPARATUS, RECORDING MEDIUM TO RETAIN PARTICLE RADIATION MONITORING PROGRAM, AND PARTICLE RADIATION MONITORING METHOD

(75) Inventors: Mitsutaka Yamaguchi, Gunma (JP); Naoki Kawachi, Gunma (JP); Takahiro Satoh, Gunma (JP); Tomihiro Kamiya, Gunma (JP); Kota Torikai, Gunma (JP); Takashi Nakano, Gunma (JP); Kazuo Arakawa, Gunma (JP); Hirofumi Shimada, Gunma (JP); Tadayuki Takahashi, Kanagawa (JP); Shin Watanabe, Kanagawa (JP); Motohide Kokubun, Kanagawa (JP)

(73) Assignee: Japan Atomic Energy Agency, Ibaraki (JP)

( * ) Notice: Subject to any disclaimer, the term of this patent is extended or adjusted under 35 U.S.C. 154(b) by 467 days.

(21) Appl. No.: 13/401,223

(22) Filed: Feb. 21, 2012

(65) Prior Publication Data
US 2012/0215495 A1   Aug. 23, 2012

(30) Foreign Application Priority Data

Feb. 22, 2011   (JP) ................. 2011-036461

(51) Int. Cl.
*G06F 19/00* (2011.01)
*G01T 1/29* (2006.01)
*A61N 5/10* (2006.01)

(52) U.S. Cl.
CPC ............. *G01T 1/29* (2013.01); *A61N 5/1048* (2013.01); *A61N 2005/1087* (2013.01)
USPC ........................................................ 702/104

(58) Field of Classification Search
CPC . G01T 1/29; A61N 2005/1087; A61N 5/1048
USPC .......................................... 702/104, 182–185
See application file for complete search history.

(56) References Cited

U.S. PATENT DOCUMENTS

| 4,059,763 | A | 11/1977 | Heighway et al. ............ 250/336 |
| 2012/0025076 | A1 | 2/2012 | Kraft .............................. 250/307 |
| 2012/0140863 | A1* | 6/2012 | Karev et al. ................... 376/157 |

FOREIGN PATENT DOCUMENTS

WO   WO 2010/115608 A2   10/2010

OTHER PUBLICATIONS

Ian E. Holloway et al.: "Reconstructive Bremsstrahlung Tomography as a Method of Imaging Pure Beta-ray Emitters in Matter" (Received Jul. 1989; revised form Aug. 1989).
D.W. Litzenberg et al.: "On-line monitoring of radiotherapy beams: Experimental results with proton beams".
Keizo Ishii.: "Continuous X-rays produced in light-ion-atom collisions" (Apr. 8, 2006).
M. Scholz.: "Heavy ion tumour therapy" (2000).

(Continued)

*Primary Examiner* — Edward Raymond
(74) *Attorney, Agent, or Firm* — Stein IP, LLC

(57) ABSTRACT

A particle radiation monitoring apparatus according to one aspect of the present invention includes a detecting unit to detect radioactive ray information of braking radiation from electrons undergoing action of particle beams incident on an irradiation body in accordance with a positional relation with the irradiation body and a calculating unit to calculate information on behaviors of the particle beams in the irradiation body from the radioactive ray information of the braking radiation corresponding to the positional relation that is detected by the detecting unit.

8 Claims, 18 Drawing Sheets

(56) References Cited

OTHER PUBLICATIONS

Chul-Hee Min et al.: "Prompt gamma measurements for locating the dose falloff region in the proton therapy" (published online Nov. 2, 2006).

Mirela Frandes et al.: "A Tracking Compton-Scattering Imaging System for Hadron Therapy Monitoring" (Manuscript received Jan. 14, 2009; revised Jun. 9, 2009. Current version published Feb. 10, 2010).

European Search Report dated Apr. 10, 2013, issued in the corresponding European Application No. 12156401.7.

Enghardt, W. et al., "The spatial distribution of positron-emitting nuclei generated by relativistic light ion beams in organic matter", Phys. Med. Biol., 1992, vol. 37, No. 11, 2127-2131.

Kabuki, S. et al., "Study on the Use of Electron-Tracking Compton Gamma-Ray Camera to Monitor the Therapeutic Proton Dose Distribution in Real Time", 2009 IEEE Nuclear Science SAymposium Conference Record, 2437-2440.

Parodi, K. et al., "PET imaging for treatment verification of ion therapy: Implementation and experience at GSI Darmstadt and MGH Boston", Nuclear Instruments and Methods in Physics Research A 591 (2008) 282-286.

Notice of Reason for Rejection dated Jul. 29, 2014, issued to corresponding Japanese Application No. 2011-036461.

\* cited by examiner

PARTICLE RADIATION MONITORING APPARATUS, RECORDING MEDIUM TO RETAIN PARTICLE RADIATION MONITORING PROGRAM, AND PARTICLE RADIATION MONITORING METHOD

CROSS-REFERENCE TO RELATED APPLICATIONS

This application claims the benefit of Japanese Application No. JP2011-036461, filed Feb. 22, 2011, in the Japanese Patent Office, the disclosure of which is incorporated herein by reference.

BACKGROUND

1. Field

Aspects of the present invention relate to technologies of a particle radiation monitoring apparatus which acquires information on behaviors of particle beams irradiated by an accelerator etc., a recording medium to retain a particle radiation monitoring program, and a particle radiation monitoring method.

2. Description of the Related Art

A technology of radiotherapy for cancer in Japan has realized the tremendous improvements of achievements in medical treatments by reducing damages to peripheral normal healthy tissues to the greatest possible degree in a way that concentrates a radiation dose on a nidus under the slogan of "Remedy without Cutting Cancer". The forefront radiotherapy for cancer has come to involve utilizing "particle therapy" which drastically reduces the radiation dose on the normal healthy tissues while irradiating an affected part with a large radiation dose and is on the verge of realizing the improvements of the achievements in medical treatments which could not be attained even by the high-level X-ray therapy. This is derived from "concentration of the radiation dose on the affected part" as a nature common to the particle beams such as proton beams and heavy particle beams. In addition, the heavy particle beams have superiority in terms of progressive migration of ions within a body and therefore exhibit a reduced deviation of the ions from a traveling direction. The heavy particle beams are also excellent in concentration of the radiation dose in a radius-vector direction with respect to the ion traveling direction, whereby a nidus of the affected part or a minute nidus part contiguous to important tissues can be precisely pinpoint-irradiated with the heavy particle beams. It is expected that an ion microsurgery technique is established as a next-generation therapy utilizing this feature of the heavy particle beams.

A pencil beam forming technology and a micro beam forming technology of converging the beams in a thin-and-narrow shape have already been developed as an accelerator or a beam technology for pinpoint-irradiating the nidus part precisely with the particle beams as described above. The particle radiation monitoring technology at the present cannot, however, monitor an internal arrival depth of the particle beams in real time, with the result that it is difficult to establish the ion microsurgery technique.

Further, a real-time monitoring technology for an energy impartation distribution (i.e., radiation dose distribution) of the nidus part undergoing the radiation therapy underway is not yet developed. Therefore, the medical treatment is performed based on a tremendous quantity of dose measurement data of a phantom through a physical or chemical technique as well as being based on a detailed therapeutic plan and empirically and clinically accumulated data. Under the present circumstances, priori confirmation of the energy impartation distribution is invariably made in the therapeutic plan and a QA (Quality Assurance) scheme, and, if there are no monitoring fluctuations of the beams during the therapeutic irradiation, the radiation therapy is carried out on the assumption that the energy distribution is reproduced and maintained. The realization of the real-time monitoring technology of the energy impartation distribution enables the medical treatment to be performed while confirming and demonstrating that the nidus part is certainly irradiated with the beams, and has an extremely large medical significance in terms of ensuring the reliability.

Further, if unpredictable filling and discharge of mucic occur in an internal cavity region during the irradiation of the particle therapy, the unpredictable filling and discharge considered by way of deviations from the therapeutic plan exert adverse influence as variations of the energy impartation distribution and the ion arrival depth. It is therefore of much benevolence to observe in real time the energy impartation distribution and the arrival depth during the irradiation of the particle beams.

In the present situation, the particle radiation monitoring techniques are exemplified (W. Enghardt et al., "The spatial distribution of positron-emitting nuclei generated by relativistic light ion beams in organic matter", Phys. Med. Biol., 1992, Vol. 37, No 11, 2127-2131) (Katia Parodi et al., "PET imaging for treatment verification of ion therapy: Implementation and experience at GSI Darmstadt and MGH Boston", Nucl. Instr. and Meth. A 591 (2008) 282-286). There is searched a technique of observing positron annihilation gamma rays defined as the gamma rays derived from positron emission nuclides (O-15, C-11, etc) generated due to the nuclear reaction between the ions and the internal atomic nucleuses and estimating an irradiation position (which will hereinafter be called a self-radiation method). As for the generation reaction of the positron emission nuclides, a majority of these nuclides are generated through not only primary reaction between the ions and the internal nuclides but also secondary reaction due to neutrons generated by the primary reaction and via complicated multiple reaction paths on the whole. Therefore, the Monte-Carlo simulation including the nuclear reaction is required for estimating a generation quantity and a generation place. Consequently, the reproduction of the energy impartation distribution from the positron distribution has a problem of requiring an analysis which traces the Monte-Carlo simulation including the complicated nuclear reaction.

Moreover, there is a time difference of several tens of seconds to several tens of minutes due to a decay period of the nuclides till the gamma rays (of, e.g., 511 keV) are emitted since the positron emission nuclides have been generated, so that a period ranging from several minutes to several tens of minutes is needed till the measurement of PET (Positron Emission Tomography) or CT (Computed Tomography) is finished since the end of the medical treatment. The positron emission nuclides migrate within the body by dint of a metabolic function inherent to a living body during this time difference. With this migration, such a problem arises that a deviation occurs between the generation position of the positron emission nuclides and the emission position of the gamma rays. This problem is called a washout effect due to the metabolism and is one of factors of complicating the prediction of the energy impartation distribution.

Measurement quantities in the particle radiation monitoring method are, e.g., the arrival depth of the particle beams and the energy impartation distribution. In the self-radiation method described above, a study for a technique of monitoring the arrival depth of the particle beams and the energy impartation distribution is advanced. In the self-radiation method, however, it is difficult to monitor in real time the arrival depth of the particle beams and the energy impartation distribution. The reason is that the positron emission nuclides generated in the self-radiation method has a problem of their being generated generally through atomic nucleus reaction exhibiting an extremely small reaction probability. Hence, a considerable period of time is expended for collecting the data required for presuming the arrival depth of the particle beams or the energy impartation distribution in the self-radiation method. To be specific, in the radiotherapy, the data required for presuming the arrival depth of the particle beams or the energy impartation distribution are obtained after finishing the medical treatment, and it is difficult to conduct the real-time monitoring during the medical treatment. Moreover, in the heavy particle beams expected for the forefront medical treatment, an irradiation quantity of the ions used for the medical treatment is approximately one tenth as small as that of proton beams, and it is further difficult to acquire the sufficient data.

Furthermore, as described above, the derivation of the quantities of the arrival depth of the particle beams and the energy impartation distribution involves the difficulty due to the intricacy of the generation reaction and the washout effect owing to the metabolism. As a technique of avoiding the washout effect, a method (which will hereinafter be called a nuclear de-excitation method) of observing the prompt gamma rays from excited atomic nucleuses generated by the atomic nucleus reaction between the particle beams and the internal atomic nucleuses is proposed (S. Kabuki et al., "Study on the Use of Electron-Tracking Compton Gamma-Ray Camera to Monitor the Therapeutic Proton Dose Distribution in Real Time", 2009 IEEE Nuclear Science Symposium Conference Record, 2437-2440).

An occurrence count of the nuclear de-excitation gamma rays is also small because of their being via the atomic nucleus reaction, and the real-time monitoring is hard to perform. In the self-radiation method, two positron annihilation beams are simultaneously generated, and it is therefore feasible to employ an imaging apparatus based on the PET and the gamma-ray pair measurement similar to the PET. In the nuclear de-excitation method, however, the single gamma ray is generated, and hence the similar apparatus cannot be used. Since the atomic nucleuses building up the internal matter are light atomic nucleuses such as hydrogen, carbon and oxygen, the nuclear de-excitation gamma rays are limited to those having the energy equal to or higher than several MeV, and there is needed the imaging apparatus for the single gamma ray exhibiting the high energy such as this. A Compton camera is proposed as the only apparatus which fulfills this requirement, however, high-energy gamma-ray defection efficiency of the Compton camera is by far smaller than the detection efficiency of the gamma rays due to the positron annihilation, and it is difficult to measure the data sufficient for presuming the arrival depth of the particle beams and the energy impartation distribution.

Herein, the monitoring of the energy impartation distribution represents a technique of directly measuring both of "internal matter density" and "ion energy". In the self-radiation method defined as the conventional method, the positron annihilation beam has only the intensity of the annihilation beam as a physical quantity for measurement because of the single energy (511 keV). Furthermore, both of the energy impartation and the annihilation beam intensity are proportional to the "internal matter density" and strongly depend on the "ion energy". To take these points into consideration, the positron annihilation method requires the assumption of the "ion energy" within the body in order to monitor the energy impartation distribution, and has such a problem that it is impossible to monitor the energy impartation distribution directly.

A conventional particle radiation monitoring method had problems which follow and could not monitor information on behaviors of the particle beams.

SUMMARY

A particle radiation monitoring apparatus according to one aspect of the present invention includes a detecting unit to detect radioactive ray information of braking radiation from electrons undergoing action of particle beams, incident on an irradiation body in accordance with a positional relation with the irradiation body and a calculating unit to calculate information on behaviors of the particle beams in the irradiation body from the radioactive ray information of the braking radiation corresponding to the positional relation that is detected by the detecting unit.

According to the configuration described above, there is detected the radioactive ray information of the braking radiation from the electrons undergoing the action of the particle beams incident on the irradiation body in accordance with the positional relation with the irradiation body. Then, according to the configuration described above, the information on the behaviors of the particle beams in the irradiation body is calculated from the radioactive ray information of the braking radiation. Herein, the radioactive ray information of the braking radiation is, e.g., a continuous energy spectral distribution of the braking radiation.

The braking radiation is of promptness and therefore has absolutely no deterioration of imaging accuracy, which is caused by the washout effect with a problem arisen in the self-radiation method. Further, the braking radiation occurs by dint of electromagnetic interaction and is therefore by far larger than by nuclear reaction (which is approximately $10^2$-fold to $10^5$-fold).

Moreover, the radioactive ray information of the braking radiation is detected as, for example, the continuous energy spectral distribution having a strong correlation with the ion energy. Hence, unlike the self-radiation method by which only the energy intensity is observed because of the annihilation beam energy being determined, in the braking radiation, it is possible to calculate the information on the behaviors of the particle beams in the irradiation body from the radioactive ray information to be detected.

Therefore, according to the configuration described above, the information on the behaviors of the particle beams can be monitored in real time.

Further, in another mode of the particle radiation monitoring apparatus according to one aspect of the present invention, the information on the behaviors of the particle beams may be an arrival depth of the particle beams.

According to the configuration described above, the information on the behaviors of the particle beams can be monitored in real time.

Still further, in still another mode of the particle radiation monitoring apparatus according to one aspect of the present invention, the information on the behaviors of the particle beams may be an energy impartation distribution of the particle beams.

According to the configuration described above, as the information on the behaviors of the particle beams, the energy impartation distribution of the particle beams can be monitored in real time.

Yet further, in yet another mode of the particle radiation monitoring apparatus according to one aspect of the present invention, the particle beams may be monochrome beams with single incident energy or Spread-Out Bragg Peak beams.

According to the configuration described above, the information on the behaviors of the monochrome beams with the single incident energy or the Spread-Out Bragg Peak beams can be monitored in real time.

It should be noted that additional modes of the particle radiation monitoring apparatus according to one aspect of the present invention may be a particle radiation monitoring method, a particle radiation monitoring program and a non-transitory computer-readable recording medium on which the particle radiation monitoring program such as this is recorded, which realize the respective configurations described above. Moreover, a still additional mode of the present invention may be a particle radiation monitoring system in which a plurality of apparatuses to realize the respective configurations described above is configured in a communication-enabled manner.

Objects and advantages of the invention will be realized and attained by means of the elements and combinations particularly pointed out in the claims.

It is to be understood that both the foregoing general description and the following detailed description are exemplary and explanatory and are not restrictive of the invention, as claimed Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Figure 1:
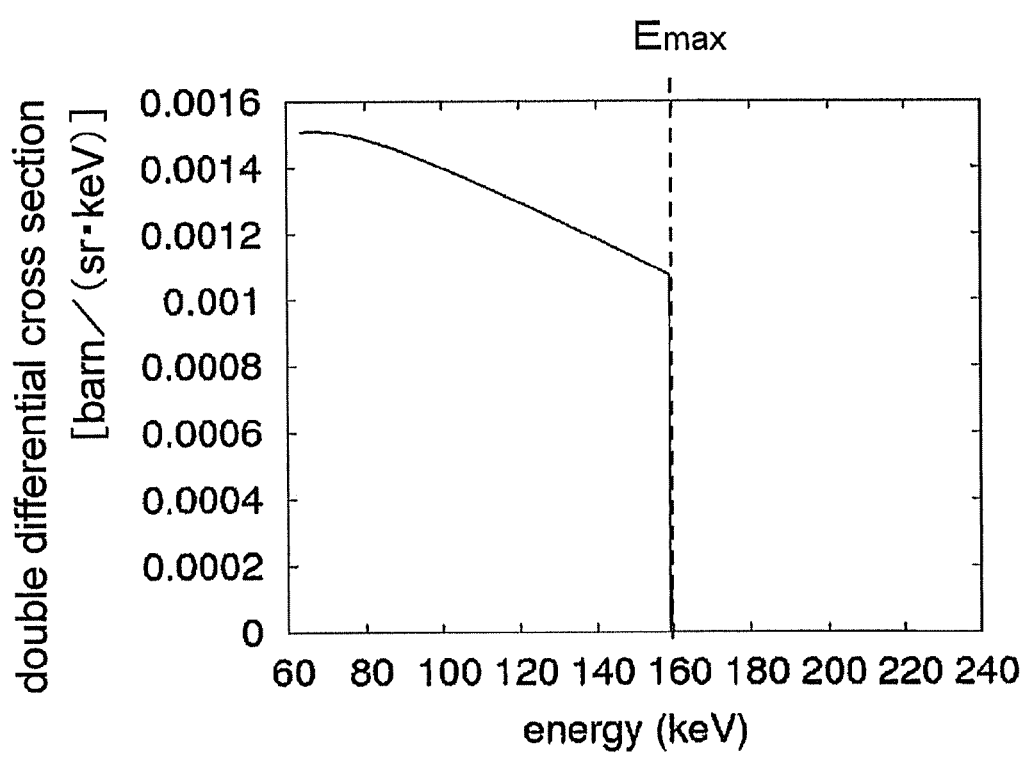
FIG. 1 is a graph illustrating energy spectrums of braking radiation.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

A particle radiation monitoring apparatus, which will hereinafter be described in detail, is given by way of embodiments (which will hereinafter be each referred to as the present embodiment) of a particle radiation monitoring apparatus, a particle radiation monitoring program and a particle radiation monitoring method according to one aspect of the present invention. The present embodiment is, however, an exemplification, and the present invention is not limited to a configuration of the present embodiment.

Note that data appearing in the present embodiment are described in a natural language, however, more specifically the data are designated by quasi-languages, commands, parameters, machine languages, etc, which are recognizable to computers.

[Outline]

The present embodiment is directed to a particle radiation real-time monitoring technique based on an observation of braking radiation (bremsstrahlung), which occurs when irradiating an irradiation body with particle beams. The braking radiation in the present embodiment represents the braking radiation that occurs from electrons given a part of energy of incident particle beams. The braking radiation is of promptness (prompt radiation). Further, the braking radiation occurs by dint of electromagnetic interaction and therefore has a reaction probability that is by far larger than by nuclear reaction (which is approximately $10^2$-fold to $10^5$-fold). Moreover, continuous energy spectrums (corresponding to radiation information of the braking radiation according to the present invention) retained by the braking radiation have a strong correlation with ion energy of the particle beams. Namely, the ion energy of the particle beams in the irradiation body can be obtained by observing the braking radiation in each position of the irradiation body. Accordingly, the present embodiment enables the particle radiation real-time monitoring to be attained by observing the braking radiation.

Note that the braking radiation, unlike gamma rays (e.g., 511 keV) and prompt gamma rays (several MeV) based on annihilation of positrons, has the comparatively low energy (in the vicinity of 50 KeV-100 KeV in the present embodiment) and has the continuous energy spectrums. Therefore, the braking radiation can be acquired in distinction from other types of energy such as the gamma rays and the prompt gamma rays based on the annihilation of the positrons.

Furthermore, the braking radiation can be classified into several types depending on occurrence factors, however, there are different energy regions in which the braking radiation occurs. Therefore, the plural types of braking radiations, even when existing in mixture, can be sorted out into the respective types.

The particle radiation monitoring can be categorized depending on a type of beams to be used and a physical quantity. The present embodiment exemplifies two types of beams such as monochrome beams and Spread-Out Bragg Peak (SOBP) beams.

Herein, the monochrome beam represents a beam of which the incident energy is monoenergetic and indicates the beam, which undergoes none of processing in terms of energy and is drawn in an intact state from an accelerator. An arrival depth, at which ions having a certain magnitude of energy are impacted into a matter, is called a range. In the case of the monochrome beams, the ranges of the ions forming the particle beams are equalized, and hence the maximum arrival depth is coincident with the range. Further, the energy imparted (transferred) by the ions has the maximum value in the vicinity of the range, and therefore the monochrome beams can attain the linear energy exhibiting high concentration, which is transferred also in a depthwise direction. A technique, called ion micro surgery, for performing a precise medical treatment by scanning point beams (over the target) exhibits effectiveness.

The SOBP beams are formed by letting the monochrome beams through a range shifter and giving continuous spread to the beam energy. The energy is not monoenergetic, and hence the range of the individual ion continuously varies, with the result that the energy imparted is of such a distribution as to have the spread in the depthwise direction.

Further, the present embodiment exemplifies two types of physical quantities of the particle beam arrival depth and the energy impartation distribution by way of the physical quantities to be measured.

The particle beam arrival depth corresponds to the range in the monochrome beams and corresponds to the range of the maximum energy ions in the SOBP beams. Information available from the particle beam arrival depth is little than from the energy impartation distribution. This information, however, enables a depthwise beam position to be monitored in real time when performing the medical treatment of the ion micro surgery, and further enables precise collimation of the irradiating position of the irradiation body and the position of the irradiation underway in the depthwise direction to be monitored in real time. Moreover, this information is useful for detecting deviation from a scheme of the medical treatment to be detected in real time.

The energy impartation distribution is a distribution plotted when measuring the energy imparted to the irradiation body (which is also called the impartation of a radiation dose or the impartation of the linear energy). In the present embodiment, the energy impartation distribution involves measuring any one of an "internal matter density" and the "energy of the particle beams (the ion energy is given by way of an example)" by use of another apparatus, or alternatively the energy impartation distribution is derived directly without inputting an assumed value and setting this value as a known value. Herein, the energy impartation distribution is in a proportionality relation with the "internal matter density". Then, a proportionality coefficient in the proportionality relation can be obtained by referring to a data table of the linear energy imparted to the irradiation body. Hence, if capable of measuring both of the "internal matter density" and the "energy of the particle beams", the energy impartation distribution can be derived. Note that the energy impartation distribution is defined as a physical quantity required to be finally derived in the particle radiation monitoring when performing the medical treatment. Hence, it is highly significant to enable the energy impartation distribution to be measured directly.

The present embodiment will hereinafter be demonstrated by sorting out the data based on the type of the particle beams and the classification of the physical quantities to be measured. It is to be noted that the irradiation particles are deemed to be ions, and the energy of the particle beams is expressed by the ion energy in the following embodiments.

First Embodiment

<Derivation>

In a first embodiment, the particle arrival depth of the monochrome beams is measured. The energy spectrums of the braking radiation have the strong correlation with the ion energy of the particle beams. To be specific, it is understood from a theoretical calculation of the braking radiation that when letting $E_{ion}$ be the ion energy, the maximum energy $E_{max}$ exist in the spectrums of the braking radiation as depicted in FIG. 1 and the maximum energy $E_{max}$ is proportional to the ion energy $E_{ion}$. FIG. 1 illustrates an example of the spectrums of the braking radiation, in which the axis of abscissas represents the energy of the braking radiation, and the axis of ordinates represents a double differential cross section (the unit is barn/(sr·keV)) of the braking radiation of quasi-free electrons. The ion energy $E_{ion}$ of the incident particles is set to 290 MeV/u, and the incident particle is C-12. As illustrated in FIG. 1, the maximum energy $E_{max}$ exists in the braking radiation and is about 160 KeV in this example.

An intensity of the braking radiation, though categorized into several types, for example, in the case of the braking radiation of the quasi-free electrons, is proportional to the double differential cross section (Phys. Rev. A 23, 24 (1981)) in [Mathematical Expression 1].

[Mathematical Expression 1]

$$\frac{d\sigma}{d\Omega d(h\omega/2\pi)} = N_T Z_p^2 \left(\frac{2\pi e^2}{hc}\right)^5$$

$$a_0^2 \frac{2m_e c^2}{T_r h\omega} \left[\sin^2\theta + \frac{1}{4}(1+p^2)(3\cos^2\theta - 1)\ln\left(\frac{1+p}{1-p}\right) - \frac{1}{2}p(3\cos^2\theta - 1)\right]$$

Herein, $p^2$ is obtained by [Mathematical Expression 2]

[Mathematical Expression 2]

$$p^2 = 1 - \frac{h\omega}{2\pi T_r}.$$

Further, $N_T$ designates the number of atoms building up the matter, $Z_P$ denotes an atomic number, $a_0$ stands for the Bohr radius, $h\omega/2\pi$ represents the energy of the braking radiation, and $\theta$ indicates an angle made by an incident direction of the ions and an emission direction of the braking radiation. The symbol e represents an elementary charge, h designates the Planck constant, c indicates the light velocity, and $m_e$ represents a mass of electron. The symbol $\sigma$ denotes an overall scattering cross section, $\Omega$ indicates a solid angle ($d\Omega=2\pi \sin\theta d\theta$), and $T_r$ represents the maximum energy of the quasi-free electrons.

Further, the maximum energy $T_r$ can be acquired by [Mathematical Expression 3]

$$T_r = \frac{m_e}{m} E_{ion} \qquad \text{[Mathematical Expression 3]}$$

In [Mathematical Expression 3], m represents a mass of ion. Based on a relation between [Mathematical Expression 1], [Mathematical Expression 2] and [Mathematical Expression 3], the double differential cross section proportional to the intensity of the braking radiation can be expressed as three variable functions of the energy $h\omega/2\pi$ of the braking radiation, the ion energy $E_{ion}$ and the emission angle θ of the braking radiation. Namely, the intensity of the braking radiation can be expressed as the function of which the variable is the energy $h\omega/2\pi$ of the braking radiation through the double differential cross section. Note that the double differential cross section proportional to the intensity of the braking radiation monotonically decreases with respect to an increase of the energy $h\omega/2\pi$ of the braking radiation.

On the other hand, in the case of the braking radiation of the quasi-free electrons, the maximum energy $E_{max}$ is obtained by [Mathematical Expression 4] ("Matter Analysis and Matter Modification Using Ion Beams" compiled by Fuminori Fujimoto and Kenichiro Komaki, published by Uchida Roukakuho Publishing Co., Ltd., pp. 81-85, chapters 1, 4 and 6).

$$E_{max} = T_r \qquad \text{[Mathematical Expression 4]}$$

The double differential cross section of the braking radiation of secondary electrons, which is given by way of another example of the braking radiation, has the same property as monotonically decreasing with respect to the increase of the energy of the braking radiation. Moreover, the braking radiation of the secondary electrons also has the same property as existence of an upper limit value $E_{max}$ in the energy of the braking radiation. The upper limit value $E_{max}$ is, however, obtained by [Mathematical Expression 5] differently from [Mathematical Expression 4] of the braking radiation of the quasi-free electrons.

$$E_{max} = 4 T_r \qquad \text{[Mathematical Expression 5]}$$

Other types of braking radiations are by far smaller in their intensities than the braking radiation of the quasi-free electrons and the braking radiation of the secondary electrons. Accordingly, the upper limit value $E_{max}$ of the energy of the braking radiation is uniquely expressed by the function of the ion energy $E_{ion}$ in [Mathematical Expression 3] through [Mathematical Expression 5], which are established in the braking radiation of the quasi-free electrons and the braking radiation of the secondary electrons. That is, when taking an inverse function of this function into consideration, the ion energy $E_{ion}$ is uniquely expressed by the function of the upper limit value $E_{max}$ of the energy of the braking radiation. Hereafter, this is expressed by [Mathematical Expression 6].

$$E_{ion} = g_{brems}(E_{max}) \qquad \text{[Mathematical Expression 6]}$$

Further, let $X_{range}$ be the range of the ions having the energy E, and the range $x_{range}$ is uniquely expressed as a function of the energy E. This will hereinafter be expressed by $$x_{range} = f_{range}(E) \qquad \text{[Mathematical Expression 7]}$$

Figure 2:
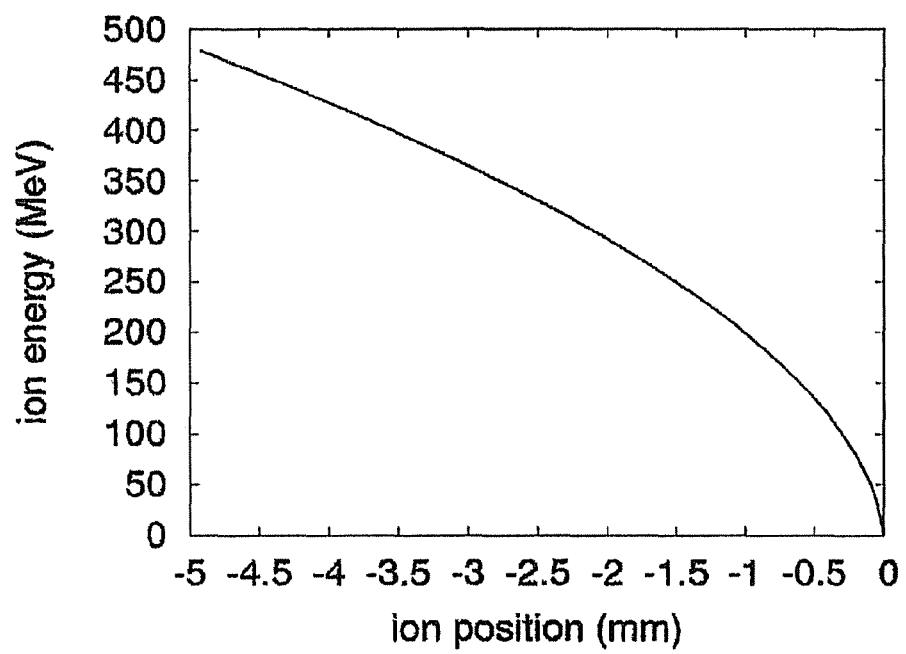
FIG. 2 is a graph illustrating ion energy in an irradiation body.

As for this [Mathematical Expression 7], i.e., as for the energy dependency of the range of the ions in the matter, there is provided a table based on the measurement values, and, for instance, this table is easily available from a calculation code package "SRIM" (refer to URL: http://www.srim.org/) created by James F. Ziegler. FIG. 2 is a graph which exemplifies the relation between the range of C-12 (carbon 12) ions and the energy. The axis of abscissas of the graph in FIG. 2 represents a relative position to an origin that is the range position, in which the beam travelling direction is positive. Further, the axis of ordinates of the graph in FIG. 2 represents the energy of the ions. According to this graph, the ion energy $E_{ion}$ in the relative position x (the beam travelling direction is positive, and the range position is the origin) from the range in the matter, is expressed by [Mathematical Expression 8].

$$E_{ion} = f_{range}^{-1}(-x)(f_{range}^{-1} \text{ is an inverse function of} \\ f_{range}, x \leq 0) \qquad \text{[Mathematical Expression 8]}$$

As depicted in FIG. 2, the ion energy $E_{ion}$ in the matter (the irradiation body) decreases as the ions get closer to the range. Furthermore, as given in [Mathematical Expression 6], there is established the proportionality relation between the ion energy $E_{ion}$, and the maximum energy $E_{max}$ of the braking radiation that is emitted from the ions. From these points, the maximum energy $E_{max}$ of the braking radiation, which is emitted from the ions, is said to decrease as the ions get closer to the range.

Accordingly, when considering the intensity of the braking radiation in a scope of a certain level of energy $E_1$ to another level of energy $E_2$ ($E_1 < E_2$) that are smaller than the maximum value of the maximum energy $E_{max}$ of the braking radiation, the maximum energy $E_{max}$ of the braking radiation emitted from the ions decreases as the irradiated ions get closer to the range, thus approaching $E_2$. With this behavior of the ions, the intensity of the braking radiation in the scope of the energy $E_1$ to the energy $E_2$ ($E_1 < E_2$) rises, i.e., an emission number of ions in the braking radiation per unit time is considered to rise. This is because the double differential cross section proportional to the intensity of the braking radiation monotonically decreases with respect to the increase of the energy $h\omega/2\pi$ of the braking radiation, so that the intensity of the braking radiation is considered to increase with respect to the decrease of the energy $h\omega/2\pi$ of the braking radiation.

Then, when the irradiated ions get still closer to the range, the maximum energy $E_{max}$ of the braking radiation, which is emitted from the ions, becomes equal to or smaller than $E_2$. At this time, when the maximum energy $E_{max}$ of the braking radiation, which is emitted from the ions, becomes equal to or smaller than $E_2$, an occurrence count of the braking radiations belonging to the scope of the energy $E_1$ to the energy $E_2$ ($E_1 < E_2$) is considered to decrease, and hence the intensity of the braking radiation in the scope of the energy $E_1$ to the energy $E_2$ ($E_1 < E_2$) is considered to reduce. Therefore, in the position where the maximum energy $E_{max}$ of the braking radiation that is emitted from the ions is E2, the intensity of the braking radiation in the scope of the energy $E_1$ to the energy $E_2$ ($E_1 < E_2$) is considered to reach its maximum.

Then, when the irradiated ions get much closer to the range, the maximum energy $E_{max}$ of the braking radiation that is emitted from the ions becomes equal to or smaller than $E_1$. At this time, when the maximum energy $E_{max}$ of the braking radiation that is emitted from the ions becomes equal to or smaller than $E_1$, the intensity of the braking radiation in the scope of the energy $E_1$ to the energy $E_2$ ($E_1 < E_2$) is considered to become "0". Hence, the intensity of the braking radiation in the scope of the energy $E_1$ to the energy $E_2$ ($E_1 < E_2$) is considered to become "0" from the position onward in which the maximum energy $E_{max}$ of the braking radiation that is emitted from the ions is $E_1$.

Figure 3:
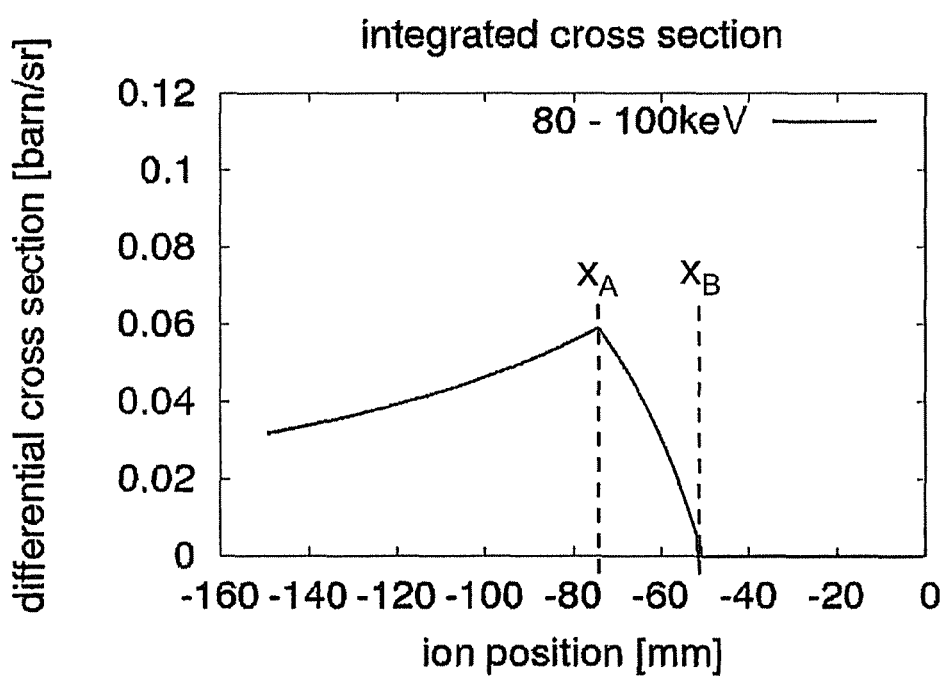
FIG. 3 is a graph illustrating a differential cross section of the braking radiation in a depthwise direction in the irradiation body, which is obtained by a theoretical formula.

Thus, when plotting the energy distribution in the depthwise direction about the intensity of the braking radiation in the scope of a certain level of energy $E_1$ to another level of energy $E_2(E_1<E_2)$, as in FIG. 3, it is understood that there appear two points (which will hereinafter be called flexing points) at which a gradient of the intensity distribution changes. FIG. 3 is a graph in which the differential cross section (a value having the proportionality relation with the intensity distribution) of the braking radiation in the depthwise direction is obtained by use of [Mathematical Expression1] and a derivation formula of the ion energy within the body. Let $x_A$, $x_B$ be positions where the first flexing point and second flexing point appear, the positions $x_A$, $x_B$ are uniquely determined by [Mathematical Expression 9] and [Mathematical Expression 10] given below in a way that employs the upper limit value $E_2$ and the lower limit value $E_1$ in the scope of the energy. Note that the upper limit value $E_2$ and the lower limit value $E_1$ in the scope of the energy in FIG. 3 are given such as $E_1$=80 keV, $E_2$=100 keV, respectively. Further, the positions $x_A$, $x_B$ are given such as $x_A$=−75 mm, $x_B$=−51 mm, respectively. The positions $x_A$, $X_B$ are respectively relative positions in which the origin is the range position, with the beam travelling direction being positive.

$$-x_A = f_{range}(g_{brems.}(E_2)) \quad \text{[Mathematical Expression 9]}$$

$$-x_B = f_{range}(g_{brems.}(E_1)) \quad \text{[Mathematical Expression 10]}$$

Values of the positions $x_A$, $X_B$ depend on each of four elements such as a structure material of the irradiation body in the vicinity of the range, the type of the particle beams, a structure material existing between a detecting unit for detecting the braking radiation from the range position and a size of the background. Therefore, a relation between these four elements and the position $x_A$ or $x_B$ is empirically measured, thereby enabling the range position to be acquired with the high accuracy. Namely, the relations given in [Mathematical Expression 9] and [Mathematical Expression 10] can be previously prepared.

Herein, $x_B$ is the position closer to the range than $x_A$. Therefore, the measurement with the higher accuracy can be expected by using the position $x_B$ than using the position $x_A$. Moreover, the ion energy increases as the ions migrate away from the range, and hence the generation of the gamma rays exhibiting the higher energy rises. Then, it follows that there augments a background effect of the gamma rays, which occurs when the gamma rays are scattered. As a consequence of this, it is presumed that the flection of the position $x_A$ actually gets hard to be distinguished. Hence, in the first embodiment, the range position is calculated by use of $x_B$. The present invention is not, however, limited to the calculation of the range position in a manner that uses the position $x_B$.

It has just been demonstrated that the derivation made so far had enabled the range position to be calculated by using $x_B$. Specifically, at first, the energy spectrums of the braking radiation, which are radiated from the ions in the irradiation body, are acquired corresponding to the position (e.g., the depthwise direction) of the irradiation body. Obtained next is such a position (distanced at $X_B$ from the range) of the irradiation body as to reach the energy $E_1$ which covers the preset maximum energy $E_{max}$ of the braking radiation that is radiated from the ions. This position is obtained by measuring the intensity of the braking radiation in the scope of the energy $E_1$ to the energy $E_2$ ($E_1<E_2$). Namely, the position (the flexing point) in which the intensity of the braking radiation in the scope of the energy $E_1$ to the energy $E_2$ ($E_1<E_2$) becomes "0" for the first time, is such a position of the irradiation body that the maximum energy $E_{max}$ of the braking radiation comes to $E_1$. Then, a specific value of $x_B$ is obtained from the energy $E_1$ by making use of an empirically already-measured relation of [Mathematical Expression 10], thus acquiring the position of the range. Through this process, in the first embodiment, there is obtained the range position, i.e., the arrival depth of the particle beams in the monochrome beams.

<Example of Configuration of Apparatus>

Figure 4:
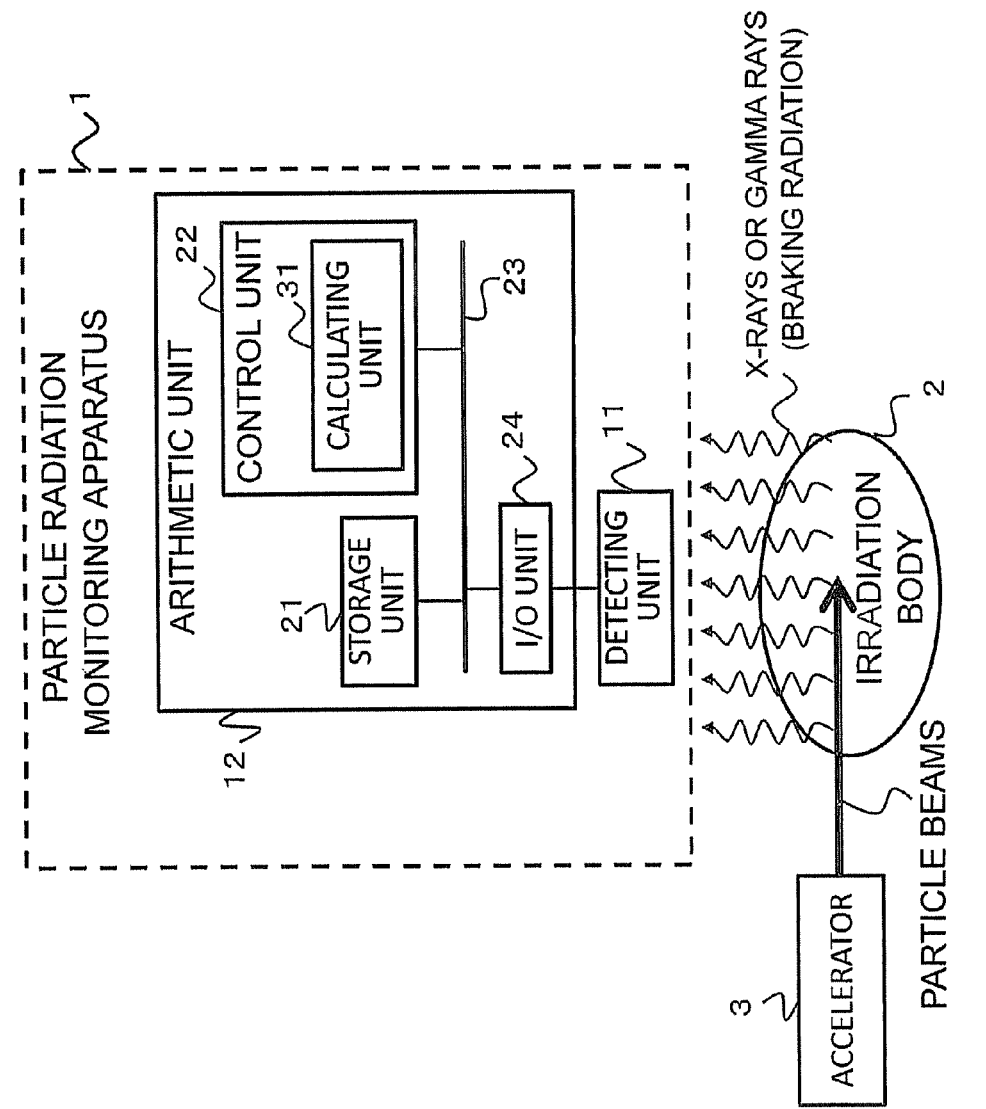
FIG. 4 is a diagram illustrating a particle radiation monitoring apparatus according to an embodiment.

Next, the particle radiation monitoring apparatus according to the first embodiment will be described. FIG. 4 illustrates the particle radiation monitoring apparatus according to the first embodiment. As illustrated in FIG. 4, the particle radiation monitoring apparatus includes a detecting unit 11 and an arithmetic unit 12. Note that the detecting unit 11 is connected in a status of being controllable by the arithmetic unit 12.

(Detecting Unit)

With respect to the particle beams emerging from an accelerator 3, the detecting unit 11 detects, correspond to the positional relation of an irradiation body 2, radioactive ray information of the braking radiation from the electrons undergoing the action from the particle beams in the irradiation body 2. The radioactive ray information of the braking radiation is defined as, e.g., the energy spectrums of at least one of X-rays and the gamma rays, which are generated by the braking radiation.

Figure 5:
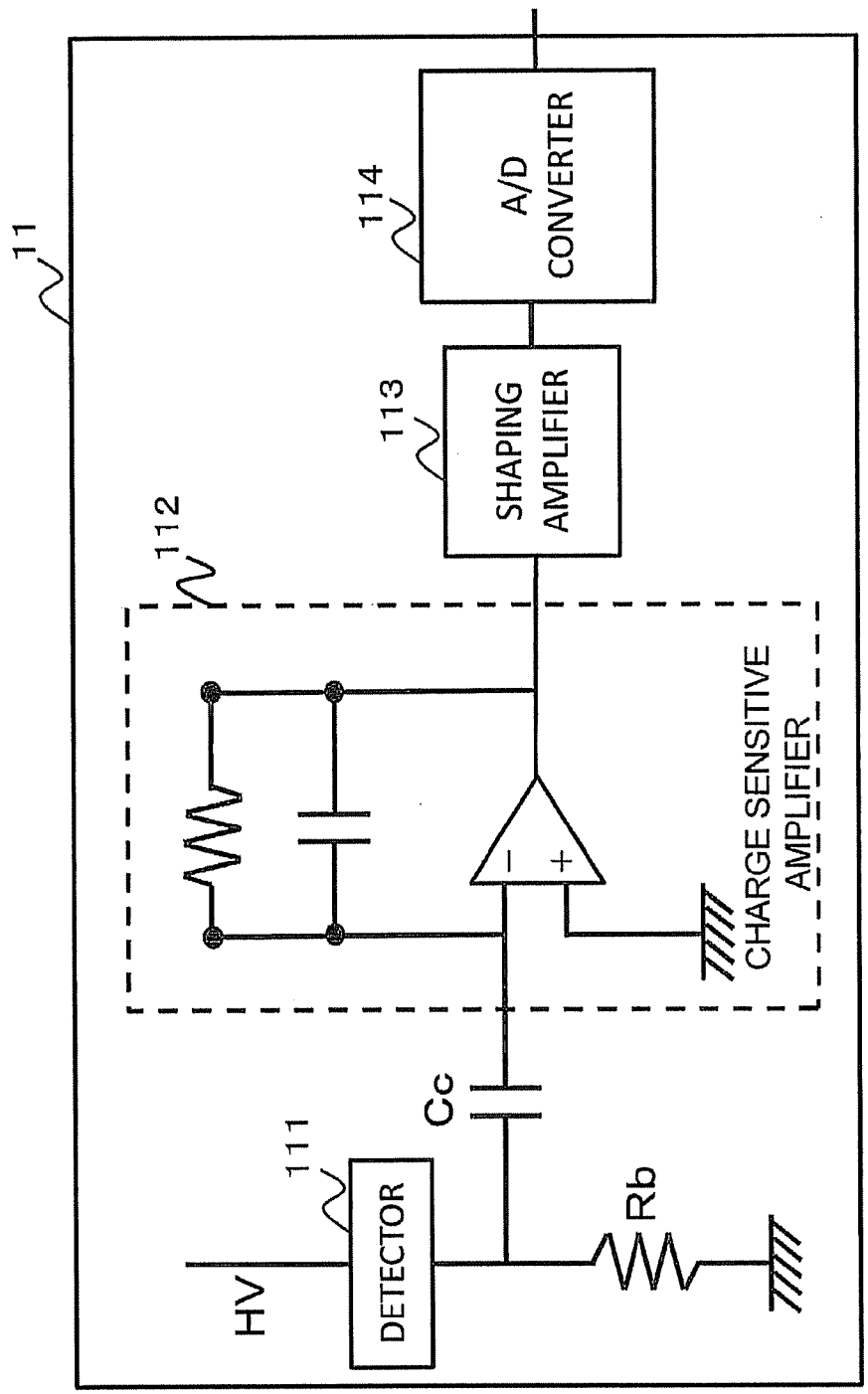
FIG. 5 is a diagram illustrating a detecting unit according to the embodiment.

FIG. 5 illustrates an example of a configuration of the detecting unit 11. As illustrated in FIG. 5, the detecting unit 11 includes a detector 111, a charge sensitive amplifier (CSA) 112, a shaping amplifier (SA) 113 and an analog/digital (A/D) converter 114.

The detector 111 is, e.g., a cadmium telluride semiconductor detector (CdTe, CdZnTe). In the first embodiment, the detector 111 may be any type of detector if capable of obtaining the energy spectrums of the incident X-rays or the gamma rays through electric signals generated by the incident X-rays or the gamma rays. As depicted in FIG. 5, the detector 111 is connected to HV (High Voltage), a coupling capacitor (Cc) and a bias resistance (Rb). With this connection, only a variation of the electric charge generated in the detector 111 is transferred to the charge sensitive amplifier 112 via the coupling capacitor.

The charge sensitive amplifier 112 reads the electric charge generated in the detector 111 and converts the electric charge into a voltage. The shaping amplifier 113 shapes a waveform of the electric signal and amplifies this signal converted into the voltage by the charge sensitive amplifier 112. Then, the A/D converter 114 reads a peak value (pulse height) of the signal.

Through the process described above, the detecting unit 11 acquires the energy spectrums of the braking radiation. More precisely, the detecting unit 11 acquires the energy spectrums containing the X-rays and the gamma rays generated by the braking radiation. Herein, as discussed above, the energy spectrums of the braking radiation can be distinguished from the energy spectrums generated due to other factors. Taking this point into consideration, the discussion will hereinafter proceed on the assumption that the detecting unit 11 acquires the energy spectrums of the braking radiation.

Figure 6A:
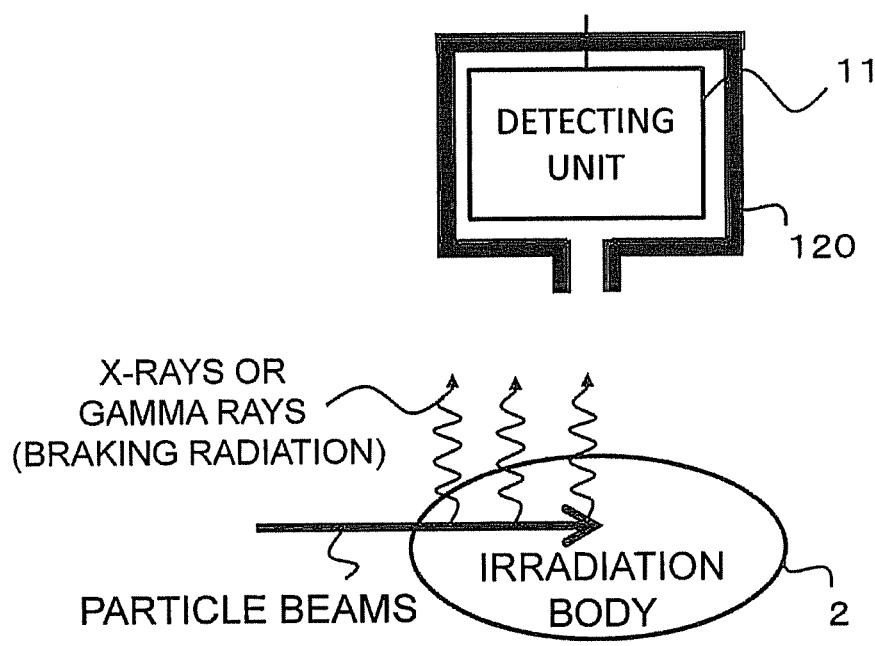
FIG. 6A is a diagram illustrating a measurement method according to the embodiment.
Figure 6B:
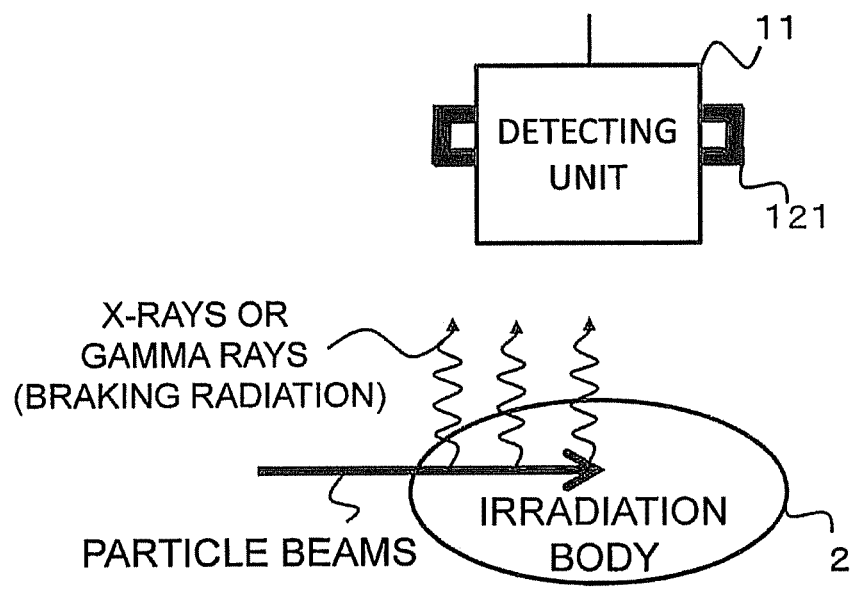
FIG. 6B is a diagram illustrating the measurement method according to the embodiment.

Further, FIGS. 6A and 6B depict measurement examples of how the detecting unit 11 detects the energy spectrums of the braking radiation in a way that corresponds to the positional relation of the irradiation body 2.

The detecting unit 11 may detect the energy spectrums of the braking radiation in accordance with the positional relation of the irradiation body 2 by further including, as illustrated in FIG. 6A, a collimator 120 which collimates the rays corresponding to the incident direction. In this case, the X-rays or the gamma rays emitted due to the irradiation of the particle beams are collimated by the collimator 120 in the position corresponding to the incident direction. Accordingly, the detector 111 provided in the detecting unit 11 can, it is preferable, measure the energy spectrums of the X-rays or the gamma rays emitted due to the irradiation of the particle beams with a much higher position resolution.

Moreover, the detecting unit 11 may detect the energy spectrums of the braking radiation in accordance with the positional relation of the irradiation body 2 by further including, as illustrated in FIG. 6B, a drive mechanism 121 controllable by the arithmetic unit 12. The drive mechanism 121 operates in a direction parallel to, e.g., the travelling direction of the particle beams. Then, the detecting unit 11 is moved by the drive mechanism 121 in the direction parallel to the travelling direction of the particle beams, thereby detecting the energy spectrums of the braking radiation in accordance with the positional relation with the irradiation body 2.

Moreover, instead of moving the detecting unit 11 by the drive mechanism 121, a plurality of detecting units 11 may be arranged. With this arrangement, a measurement error due to time fluctuations of the background can be cancelled, and the highly accurate measurement can be attained.

Note that the detecting unit 11 in FIGS. 6A and 6B may also be the detector 111. The detecting unit 11 may be equipped with the detector 111 including the collimator 120 or the drive mechanism 121 as depicted in FIG. 6A or 6B.

(Arithmetic Unit)

Next, the arithmetic unit 12 will be described. The arithmetic unit 12 obtains information on behaviors of the particle beams in the irradiation body from the radioactive ray information of the braking radiation corresponding to the positional relation detected by the detecting unit 11. As depicted in FIG. 4, the arithmetic unit 12 includes, as a hardware configuration, existing hardware components such as a storage unit 21, a control unit 22 and an input/output unit 24, which are connected via a bus 23.

The storage unit 21 is, e.g., a hard disk. A variety of data and programs used in processes executed by the control unit 22 are stored on the storage unit 21. In the first embodiment, the empirically already-measured relation in [Mathematical Expression 10], which is described in the derivation given above, i.e., the corresponding relation between the energy $E_1$ and the position $x_B$ is further stored on the storage unit 21.

The control unit 22 is a single or a plurality of processors such as a microprocessor(s) or a CPU(s) (Central Processing Unit(s)), and includes peripheral circuits (ROM (Read Only Memory), RAM (Random Access Memory), interface circuit, etc) used in processes of the processor.

The I/O unit 24 is exemplified by a USB (Universal Serial Bus) or a LAN (Local Area Network) and is defined as an interface for inputting and outputting the data. In the first embodiment, the arithmetic unit 12 is connected via the I/O unit 24 to the detecting unit 11. For example, the control unit 22 included in the arithmetic unit 12 controls the detecting unit 11 via the I/O unit 24. More specifically, for instance, the program etc stored on the storage unit 21 is deployed on the RAM etc defined as the peripheral circuit of the control unit 22 and is executed by the processor of the control unit 22, and the electric signal generated by this execution is transferred to the detecting unit 11 via the I/O unit 24. The detecting unit 11 is thereby controlled by the control unit 22.

Note that the arithmetic unit 12 may be configured by a general-purpose computer such as a PC (Personal Computer).

As illustrated in FIG. 4, the control unit 22 includes a calculating unit 31. The calculating unit 31 is realized in such a way that the program etc stored on the storage unit 21 is deployed on the RAM etc defined as the peripheral circuit to the control unit 22 and executed by the processor of the control unit 22.

The calculating unit 31 obtains the information on the behaviors of the particle beams in the irradiation body from the radioactive ray information of the braking radiation corresponding to the positional relation detected by the detecting unit 11. In the first embodiment, the calculating unit 31 obtains, based on the derivation given above, the arrival depth of the particle beams in the monochrome beams.

To be specific, at first, the detecting unit 11, in the way of being controlled by the control unit 22, acquires the energy spectrums of the braking radiation, which are generated by the monochrome beams, corresponding to the position of the irradiation body. Next, the calculating unit 31 obtains the intensity of the braking radiation in the scope of the energy $E_1$ to the energy $E_2$ ($E_1<E_2$) from the energy spectrums acquired by the detecting unit 11. Then, the calculating unit 31 obtains the position (flexing point) where the intensity of the braking radiation in the scope of the energy $E_1$ to the energy $E_2$ ($E_1<E_2$) becomes "0" for the first time from the energy $E_1$. This position is the position of the irradiation body, in which the maximum energy $E_{max}$ of the braking radiation comes to $E_1$ set as the parameter by the program etc stored on the storage unit 21. Finally, the calculating unit 31 obtains a value of the specific position $x_B$ from $E_1$ by use of the corresponding relation between $E_1$ and $x_B$, which is stored on the storage unit 21, thus obtaining the position of the range. Through this process, the calculating unit 31 obtains the range position, i.e., the arrival depth of the particle beams in the monochrome beams.

Operational Example

Figure 7:
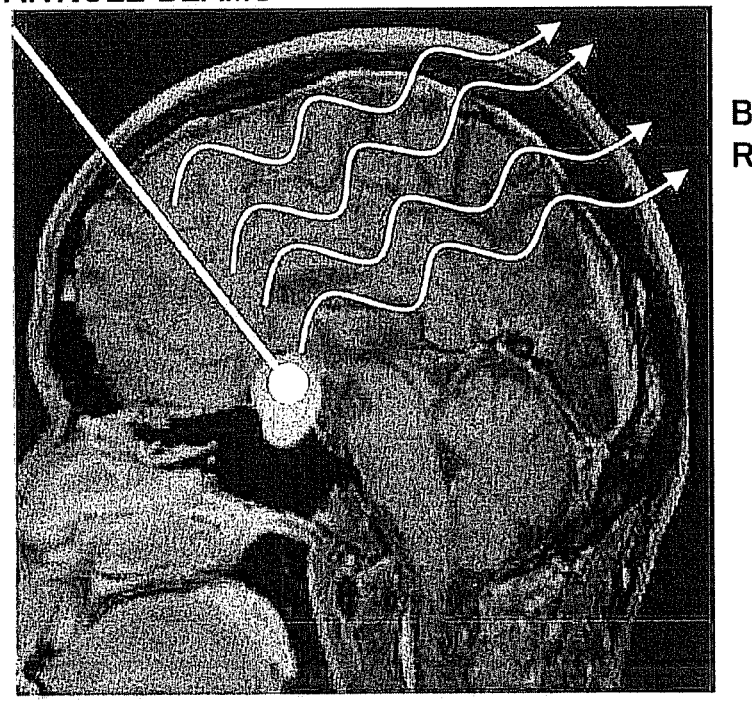
FIG. 7 is a schematic diagram of hypophyseal adenoma therapy based on heavy particle beams.

Next, an operational example in the first embodiment will be described. FIG. 7 illustrates an example of a medical treatment for hypophyseal adenoma by using heavy particle beams. The present operational example illustrates an operation of real-time monitoring of the particle beams in a manner that simulates conditions for the medical treatment for the hypophyseal adenoma by use of the heavy particle beams such as this depicted in FIG. 7 in order to demonstrate the feasibility in the first embodiment.

Figure 8:
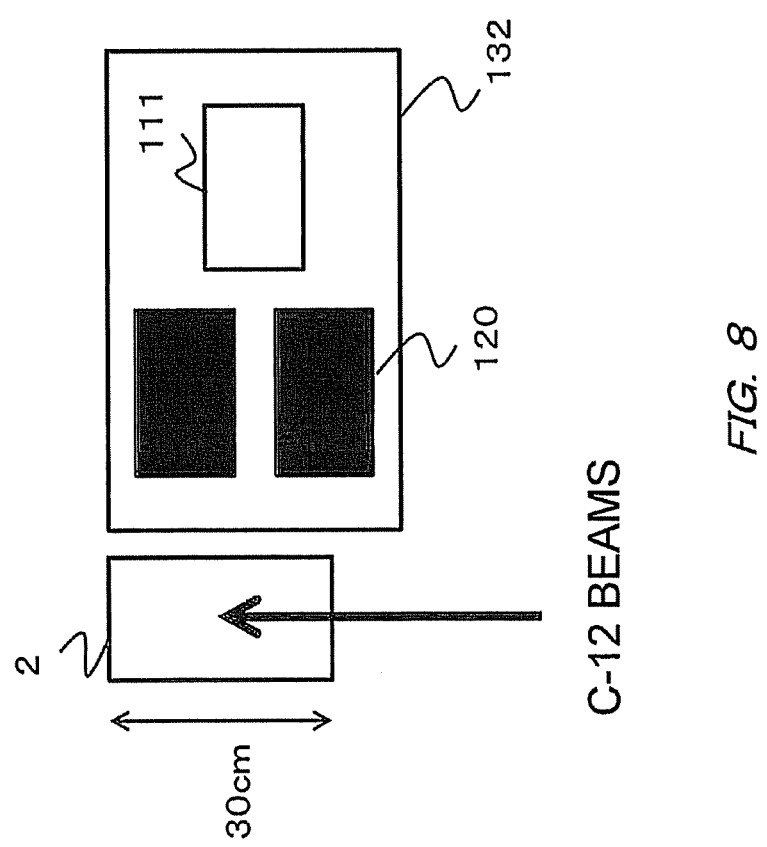
FIG. 8 is a diagram illustrating a detector in an operational example in a first embodiment.

An affected part of the hypophyseal adenoma exists deep in the body, and therefore the particle beams having the energy of about 290 MeV/u are employed as the particle beams irradiated from the accelerator 3. FIG. 8 depicts an example of the detector 111 which measures the energy spectrums of the braking radiation generated from the vicinity of the range with the irradiation of the particle beams in the present operational example. The carbon monochrome beams exhibiting the energy of 290 MeV/u are made to enter the irradiation body 2 (which is water phantom in the present operational example), in which the energy spectrums of the braking radiation are measured by employing the collimator 120 composed of lead and the detector 111, i.e., the cadmium telluride semiconductor detector. The water phantom used herein is configured by pouring the water into an acrylic cylindrical phantom having a thickness of 30 cm in a beam-axial direction and a diameter of 10 cm in the direction vertical to the beam axis. The lead collimator 120 and the detecting unit 11 including the detector 111, i.e., the cadmium telluride semiconductor detector are installed in the vicinity of the water phantom, in which the spectrums are measured by moving the detecting unit 11. Further, a shield block against neutrons is installed in the periphery of the detector 111 in order to eliminate influence of thermal neutrons upon the semiconductor detector.

Figure 9:
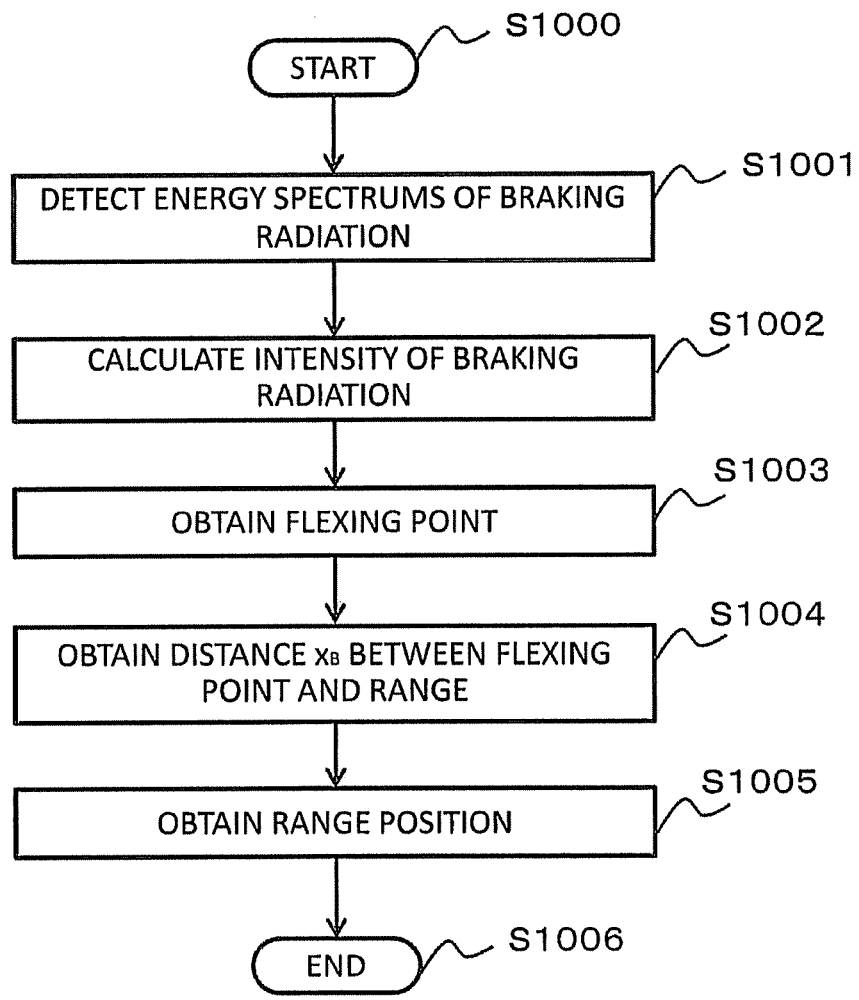
FIG. 9 is a flowchart illustrating a procedure of measuring an arrival depth (range position) of particle beams in carbon monochrome beams in the first embodiment.

FIG. 9 depicts a procedure of measuring the arrival depth (range position) of the particle beams in the carbon monochrome beams in the present operational example.

For instance, a start of the measurement is triggered by the control unit 22 executing the program etc stored on the storage unit 21 on the basis of the operation information of the user via an unillustrated user interface provided in the arithmetic unit 12 (S1000).

Upon starting the measurement, the detecting unit 11, which is controlled by the control unit 22 of the arithmetic unit 12, detects the energy spectrums of the braking radiation emitted in a 90° direction to the ion travelling direction, corresponding to a positional relation with the water phantom (S1001).

Next, the calculating unit 31 calculates the intensity of the braking radiation in a predetermined energy scope with respect to each position of the water phantom by employing the detected energy spectrums of the braking radiation (S1002). The energy scope is set by use of parameters etc of the program etc stored on the storage unit 21. In the present operational example, the energy scope is set to the scope of 68±5 keV. This is because the energy scope is on a par with the X-rays or the gamma rays of TI-201 (thallium 201) that is generally used as a radiation medicine for diagnosis, and is generally known as the energy scope in which the highly accurate measurement can be done.

Next, the calculating unit 31 obtains the flexing point by using the intensity of the braking radiation in the predetermined energy scope that is calculated on a per-position basis of the water phantom (S1003). For example, the calculating unit 31 obtains the flexing point by graphing the intensity of the braking radiation that is calculated along the carbon monochrome beams in the way of being associated with the positional relation in the direction along the carbon monochrome beams (as will be stated later on in FIG. 11).

Subsequently, the calculating unit 31 obtains the distance $x_B$ between the flexing point and the range by employing the lower limit value $E_1$ of the predetermined energy scope used for calculating the intensity of the braking radiation (S1004). The distance $x_B$ is obtained by using the empirically measured result as described above. The calculating unit 31 obtains the distance $x_B$ by using the empirically-already-measured relation of [Mathematical Expression 10] that is stored on the storage unit 21, i.e., the corresponding relation between $E_1$ and $x_B$.

Next, the calculating unit 31 obtains, as a position of the range, a position to which the ions travel just an absolute value $x_B$ in the travelling direction of the carbon monochrome beams from the flexing point (S1005). The position of the range is thus calculated, and this measurement is finished (S1006).

Figure 10:
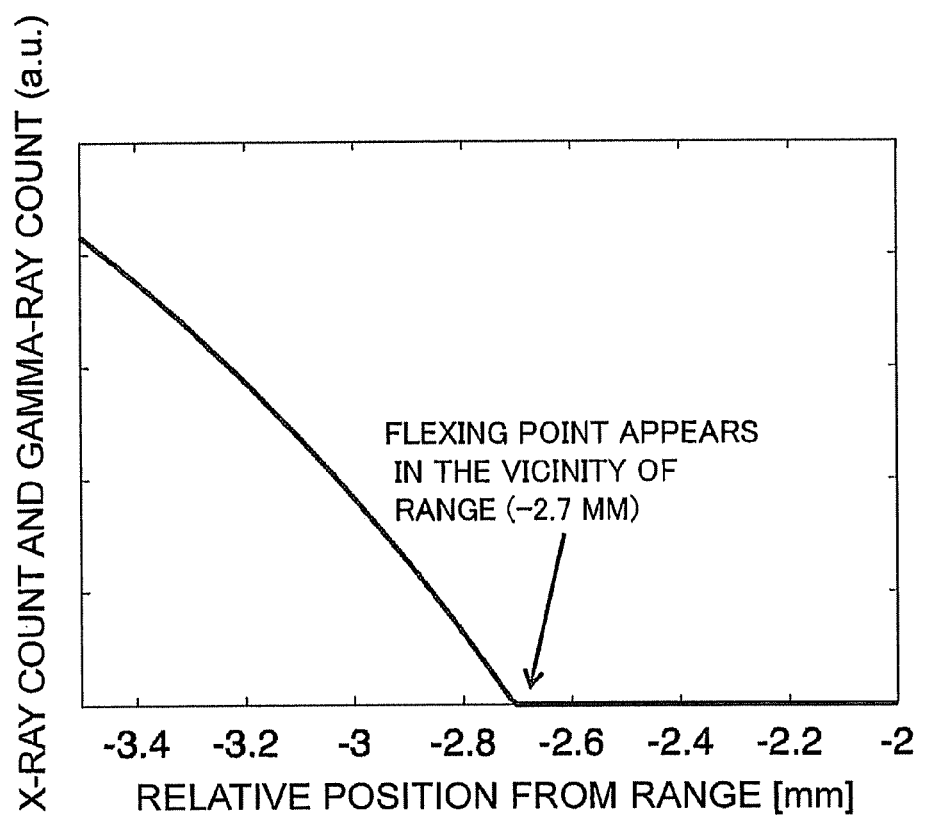
FIG. 10 is a diagram illustrating a result of theoretically calculating intensity of the braking radiation of 68±5 keV, which is emitted in a 90° direction to an ion travelling direction in the first embodiment.

Note that FIG. 10 depicts a result of calculating the intensity of the braking radiation of 68±5 keV that is emitted in the 90° direction to the ion travelling direction by use of [Mathematical Expression 1]. FIG. 10 aims at only obtaining the position of the flexing point in terms of a theoretical value, and hence there is employed the formula ([Mathematical Expression 1]) of the quasi-free electron braking radiation, which is easy to be calculated, as the formula of the double differential cross section. As a matter of fact, the secondary electron braking radiation is dominant in the braking radiations. The behaviors of the braking radiation energy of the double differential cross section do not, however, exhibit a large difference between the secondary electron braking radiation and the quasi-free electron braking radiation. Further, the formation of the flexing point is derived from the existence of the upper limit of the braking radiation energy, and therefore the upper limit value of the double differential cross section involves using an accurate value (a value of the secondary electron braking radiation). The axis of abscissas represents a relative position in which the range position is "0". Further, the ions travel in the plus direction from the minus direction (from left to right). The axis of ordinates represents the intensity (X-ray count and gamma-ray count) of the braking radiation. The flexing point $x_B$ appears in the relative position distanced at about −2.7 mm from the range.

Figure 11:
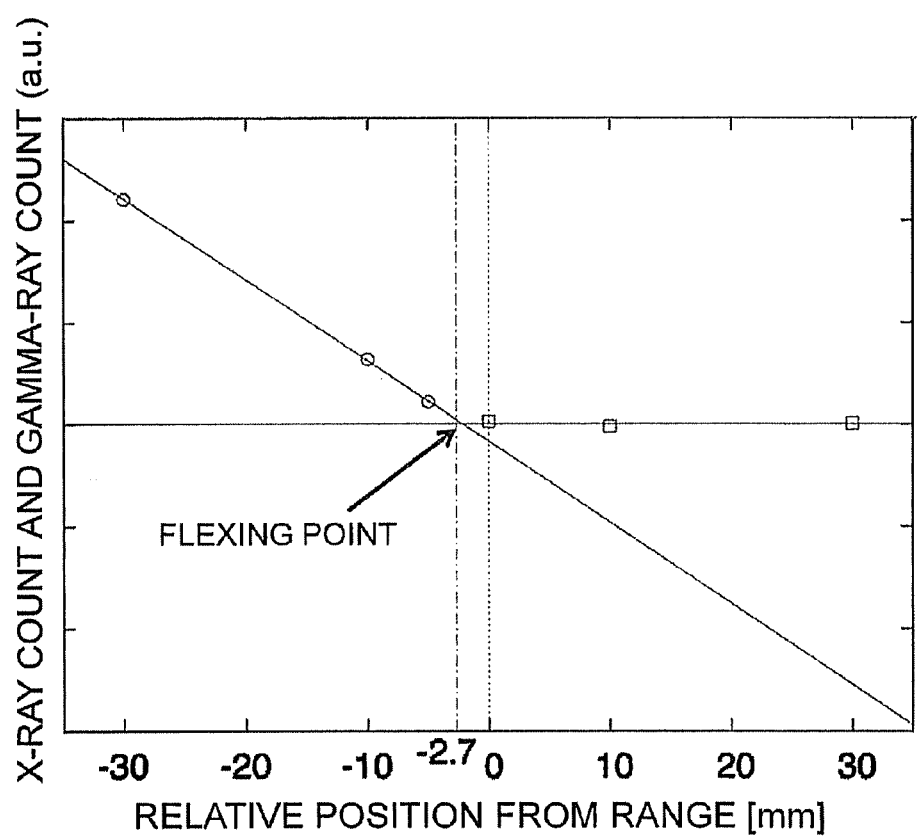
FIG. 11 is a diagram illustrating a result of measuring depthwise direction dependency of the intensity (X-ray count and gamma-ray count) of the braking radiation of 68±5 keV in the first embodiment.

Moreover, FIG. 11 illustrates a result of measuring depth-wise direction dependency of the intensity (X-ray count and gamma-ray count) of the braking radiation of 68±5 keV in S1003. It is feasible to confirm the flexing point presumed in FIG. 10. Derivation of the position of the flexing point involves fitting a data point (mark "○" in FIG. 11) serving as the background by a straight line with a gradient "0", fitting remaining data points (mark "□" in FIG. 11) by a low-order polynomial function and setting an intersection between obtained two lines as the flexing point. When the position $x_B$ of the flexing point is obtained from the fitting result, the relative position from the range becomes −2.2 mm. This has no discrepancy from the theoretical value "−2.7 mm" with an error of 0.5 mm. Namely, this implies that the range can be empirically calculated with the error of approximately 0.5 mm.

There is a difference in shape of the function in the minus-sided region of the relative position between the theoretical calculation (FIG. 10) and the empirical result (FIG. 11), however, this is because, it is considered, the theoretical calculation ignores an effect that the high-energy gamma rays are increasingly generated due to the rise in ion energy as the ions get away from the range.

Second Embodiment

Next, a second embodiment will be described. The second embodiment involves measuring the arrival depth of the particle beams in the SOBP beams.

<Derivation>

The SOBP beams have a continuous distribution of the ion energy due to a range shifter. With this distribution, in the SOBP beams, the ions having the low energy stop more frontward of the irradiation body, and the ions having the maximum energy form the characteristic points. The characteristic point, though appearing as the "flexing point of the intensity (X-ray count and the gamma-ray count) of the braking radiation" in the first embodiment, is observed as a "flexing point of a "first-order derivative of the intensity (X-ray count and the gamma-ray count) of the braking radiation" in the second embodiment. The reason is given as follows.

The SOBP beams are the superposed beams of the monochrome beams having the different energy, and it is therefore considered that the intensity (X-ray count and the gamma-ray count) of the braking radiation emitted from the SOBP beams is a sum (integral) of the intensities of the braking radiations emitted from the monochrome beams having respective levels of energy. A distribution of the intensities of the braking radiations emitted by the monochrome beams having different levels of energy, is expressed in the form of moving leftward in parallel the intensity distribution (e.g., FIG. 10) of the braking radiation emitted by the monochrome beams having the maximum energy. Hence, the intensity of the braking radiation in the SOBP beams takes a superposed shape while moving leftward in parallel the intensity distribution (e.g., FIG. 10) in the case of the monochrome beams having the maximum energy.

Herein, let $N_{mono}(x)$ be a graph in FIG. 10, and $N_{mono}(x)$ is expressed in [Mathematical Expression 11] through [Mathematical Expression 13]. Note that C is a constant.

$$N_{mono}(x)=C, \text{ where } x>x_B \quad \text{[Mathematical Expression 11]}$$

However;

$$N_{mono}(x)=h(x), \text{ where } x \leq x_B \quad \text{[Mathematical Expression 12]}$$

However;

$$h(x_B)=C. \quad \text{[Mathematical Expression 13]}$$

When using $N_{mono}(x)$ an intensity "$N_{SOBP}(x)$" of the braking radiation in the SOBP beams is expressed as by [Mathematical Expression 14].

$$N_{SOBP}(x)=\int_x^{x_0} N_{mono}(x')dx'=A-\int_{x_B}^x N_{mono}(x+)dx'. \quad \text{[Mathematical Expression 14]}$$

where $x_0$ and A are constants. Then, the first-order derivative of $N_{SOBP}(x)$ is expressed by [Mathematical Expression 15].

[Mathematical Expression 15]

$$\frac{dN_{SOBP}(x)}{dx} = \frac{dA}{dx} - \frac{d}{dx}\int_{x_B}^x N_{mono}(x')dx' = -N_{mono}(x).$$

Namely, in the case of the SOBP beams, the first-order derivative takes the same form (the sign is reversed), so that the flexing point appears in the first-order derivative of the intensity of the braking radiation.

For the reason given above, in the second embodiment, the characteristic point is observed as the "flexing point of the first-order derivative of the intensity (X-ray count and the gamma-ray count) of the braking radiation". The position $x_B$ of the flexing point is expressed in the same way as in the case ([Mathematical Expression 10] of the first embodiment.

$$-x_B=f_{range}(g_{brems.}(E_1)) \quad \text{[Mathematical Expression 16]}$$

Accordingly, the arrival depth of the particle beams can be monitored based on the measurement of the flexing point by the same method as in the first embodiment.

<Example of Configuration of Apparatus and Operational Example>

An example of a configuration of the particle radiation monitoring apparatus in the second embodiment is the same as the example, depicted in FIG. 4, of the configuration of the apparatus in the first embodiment. The calculating unit 31 in the second embodiment, however, obtains the first-order derivative of the intensity of the braking radiation instead of obtaining the intensity of the braking radiation in S1002 in FIG. 9.

Figure 12A:
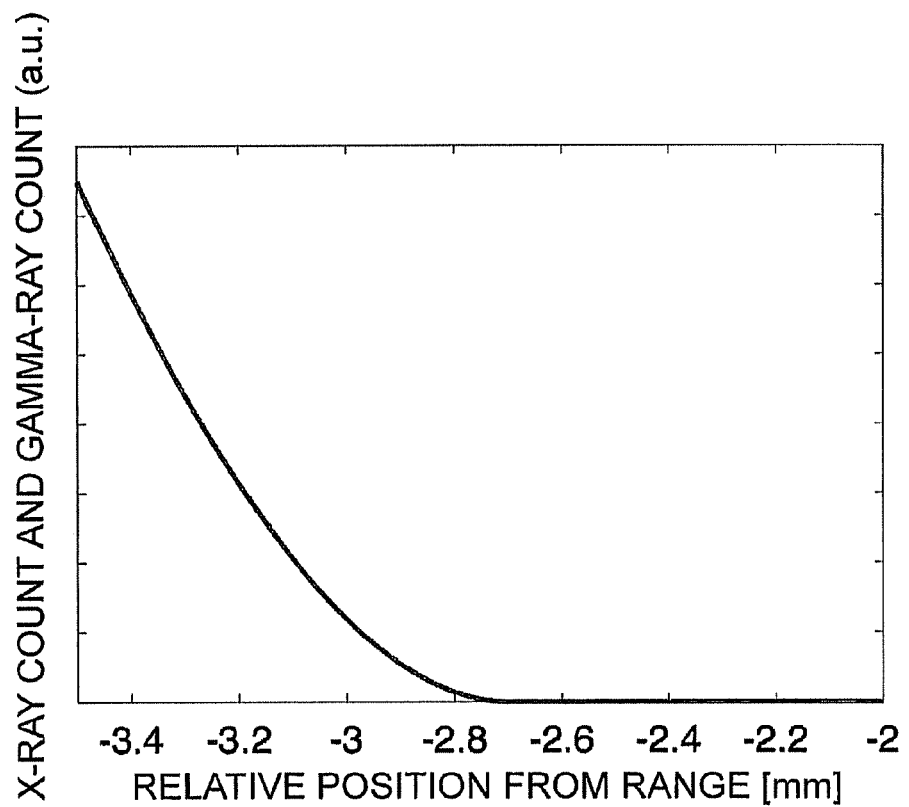
FIG. 12A is a diagram depicting a result of theoretically calculating the intensity of the braking radiation having 68±5 keV that is emitted in the 90° direction to the ion travelling direction in a second embodiment.

Note that FIG. 12A depicts a graph plotted by calculating the intensity of the braking radiation having 68±5 keV that is emitted in the 90° direction to the ion travelling direction. The axis of abscissas represents a relative position in which the range position is "0". Further, the ions travel in the plus direction from the minus direction (from left to right). The axis of ordinates represents the intensity (X-ray count and gamma-ray count) of the braking radiation.

Figure 12B:
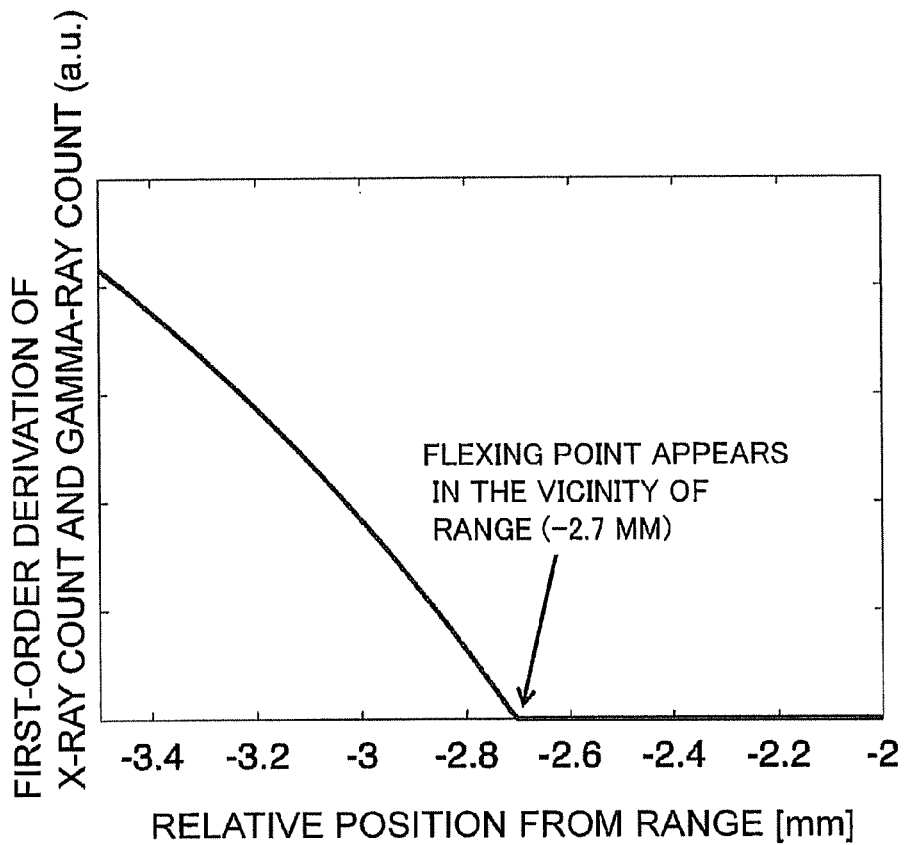
FIG. 12B is a diagram illustrating a result of what the graph in FIG. 12A undergoes first-order derivation with respect to a relative position.

Further, FIG. 12B illustrates what the graph in FIG. 12A undergoes the first-order derivation with respect to the relative position. As illustrated in FIG. 12B, the flexing point appears in the relative position distanced at approximately −2.7 mm from the range. Accordingly, in the second embodiment also, the arrival depth of the particle beams can be monitored by measuring the flexing point.

Third Embodiment

Next, a third embodiment will be described. The third embodiment involves measuring an energy impartation distribution of the monochrome beams.

<Derivation>

The "intensity of the braking radiation" is proportional to the "internal matter density". The proportionality coefficient, however, differs depending on the ion energy of the particle beams. The proportionality coefficient can be obtained from a theoretical cross section of the braking radiation. Further, the proportionality coefficient can be measured by a priori experiment. The "internal matter density" can be thereby easily drawn out of the "intensity of the braking radiation".

Herein, as stated in the first embodiment, the ion energy of the particle beams can be acquired from the maximum energy of the braking radiation (or the spectral shape of the braking radiation). With this acquisition, the proportionality coefficient between the "intensity of the braking radiation" and the "internal matter density" can be determined. Moreover, the "intensity of the braking radiation" can be obtained from the spectrums of the braking radiation. Namely, the "internal matter density" can be obtained by detecting or measuring the energy spectrums of the braking radiation.

Accordingly, the energy spectrums of the braking radiation are detected or measured on the per-position basis of the irradiation body, thereby enabling the "internal matter density" to be obtained on the per-position basis of the irradiation body. The "internal matter density" is in the proportionality relation with the impartation of the energy. The proportionality coefficient thereof can be acquired by referring to a linear energy impartation data table with respect to the irradiation body. Hence, the "energy impartation distribution" can be obtained from the "internal matter density" on the per-position basis of the irradiation body. Note that a complete set of this data table has already been prepared and opened to the public as the calculation code package "SRIM" (refer to URL: http://www.srim.org/) created by James F. Ziegler.

To summarize the derivation made above, the energy impartation distribution can be obtained by detecting or measuring the energy spectrums of the braking radiation on the per-position basis of the irradiation body.

<Example of Configuration of Apparatus>

A configuration of the particle radiation monitoring apparatus according to the third embodiment is the same as the example, depicted in FIG. 4, of the configuration of the apparatus in the first embodiment.

In the particle radiation monitoring apparatus according to the third embodiment, however, the information on the proportionality coefficient between the "intensity of the braking radiation" and the "internal matter density", which are associated with the ion energy of the incident particle beams, is stored on the storage unit 21. Further, the linear energy impartation data table with respect to the irradiation body, i.e., the information on the proportionality coefficient between the "internal matter density" and the energy impartation, is stored on the storage unit 21.

Then, in the particle radiation monitoring apparatus according to the third embodiment, the calculating unit 31 obtains, based on the derivation described above, the energy impartation distribution of the monochrome beams.

To be specific, to begin with, the detecting unit 11 is controlled by the control unit 22 and thus acquires the energy spectrums of the braking radiation that are generated by the monochrome beams, corresponding to the position of the irradiation body. Next, the calculating unit 31 calculates the intensity of the braking radiation from the energy spectrums of the braking radiation, which are acquired by the detecting unit 11. Further, the calculating unit 31 calculates the maximum energy of the braking radiation from the shape of the energy spectrums of the braking radiation, which are acquired by the detecting unit 11. Then, the calculating unit 31 acquires a distribution of the internal matter density in every position of the irradiation body by using the ion energy obtained from the maximum energy of the braking radiation, the information, stored on the storage unit 21, on the proportionality coefficient between the "intensity of the braking radiation" and the "internal matter density", which are associated by the ion energy, and the intensity of the braking radiation. Finally, the calculating unit 31 calculates the energy impartation distribution by employing the distribution of the internal matter density and the information, stored on the storage unit 21, on the proportionality coefficient between the "internal matter density" and the energy impartation.

Note that in the case of obtaining a three-dimensional energy impartation distribution, the detecting unit 11 is changed to a device (a Compton camera) capable of 3D imaging.

Operational Example

Figure 13:
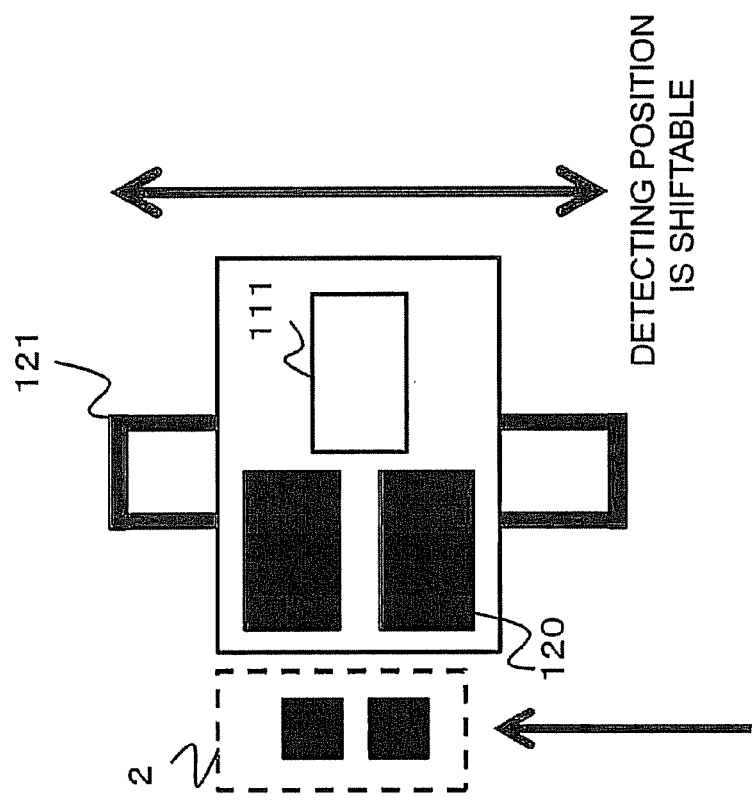
FIG. 13 is a diagram illustrating a detector in an operational example in a third embodiment.

Next, an operational example of the third embodiment will be described. FIG. 13 illustrates an example of the detector 111 which measures the energy spectrums of the braking radiation generated from the vicinity of the range with the irradiation of the particle beams in the present operational example. The monochrome beams for the irradiation involve using the carbon monochrome beams of which the energy is about 290 MeV/u similarly to the operational example of the first embodiment.

Moreover, in the present operational example, the acryl provided with a gap of about 8 mm is used as the irradiation body 2 in order to demonstrate that the energy impartation distribution can be obtained. It is considered that the braking radiation occurs from the acryl but does not almost occur from the gap (air). Therefore, the energy impartation distribution in the relation such as this is obtained, thereby demonstrating that the energy impartation distribution can be calculated by the technique based on the third embodiment.

Then, the detector 111 which measures the energy spectrums of the braking radiation involves using the cadmium telluride semiconductor detector with a width of 5 mm, of which the detecting position is shiftable by the drive mechanism 121, the detector being provided with the lead collimator 120 having a slit width of 2 mm. Note that the origin of the detecting position is set to the center of the gap, and the travelling direction of the carbon monochrome beams is set positive.

Figure 14:
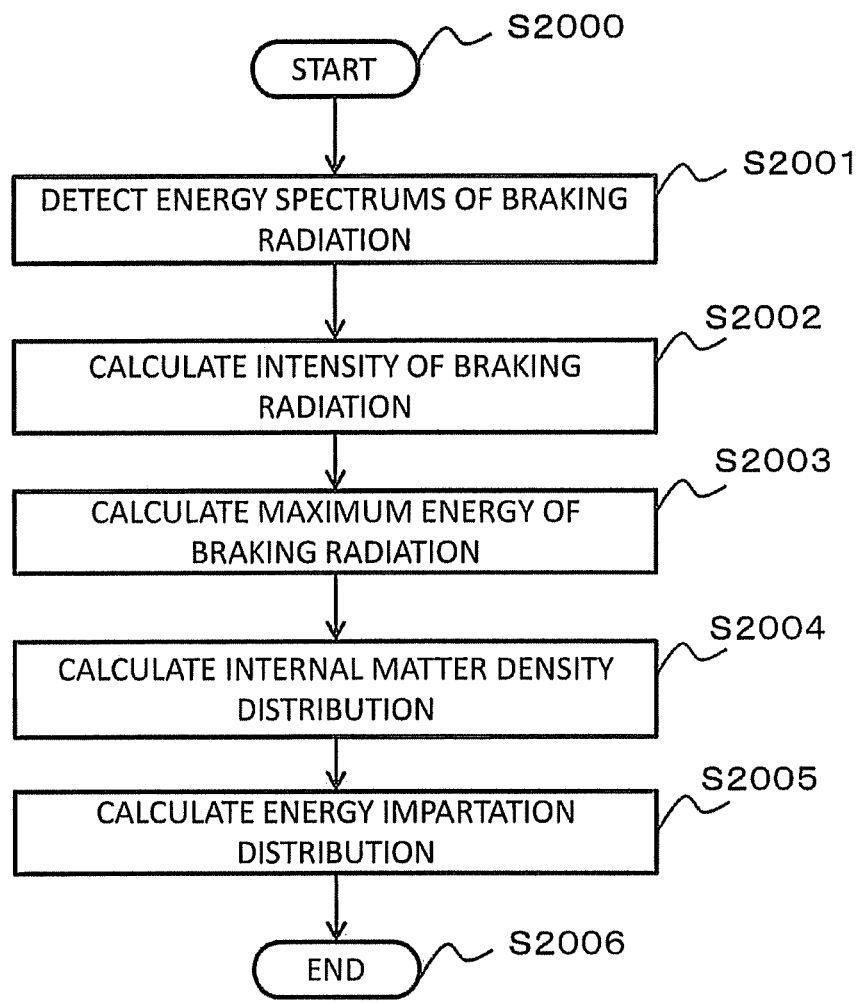
FIG. 14 is a flowchart illustrating a procedure of measuring an energy impartation distribution of carbon monochrome beams in the third embodiment.

FIG. 14 illustrates a procedure of measuring the energy impartation distribution of the carbon monochrome beams in the present operational example.

For example, a start of the measurement is triggered by the control unit 22 executing the program etc stored on the storage unit 21 on the basis of the operation information of the user via an unillustrated user interface provided in the arithmetic unit 12 (S2000).

Upon starting the measurement, the detecting unit 11 controlled by the control unit 22 of the arithmetic unit 12 detects the energy spectrums of the braking radiation emitted in the 90° direction to the ion travelling direction, corresponding to the positional relation of the acryl having the gap (S2001).

Next, the calculating unit 31 calculates the intensity of the braking radiation from the energy spectrums of the braking radiation, which are acquired by the detecting unit 11 (S2002). In the present operational example, an integral value of the scope of 30 KeV through 60 KeV is set as the intensity of the braking radiation.

Subsequently, the calculating unit 31 calculates the maximum energy of the braking radiation from the shape of the energy spectrums of the braking radiation, which are acquired by the detecting unit 11 (S2003).

Next, the calculating unit 31 obtains the distribution of the internal matter density in every position of the acryl having the gap by employing the ion energy acquired from the maximum energy of the braking radiation, the information, stored on the storage unit 21, on the proportionality coefficient between the "intensity of the braking radiation" and the "internal matter density", which are associated by the ion energy, and the intensity of the braking radiation (S2004).

Subsequently, the calculating unit 31 calculates the energy impartation distribution by use of the distribution of the internal matter density and the information, stored on the storage unit 21, on the proportionality coefficient between the "internal matter density" and the energy impartation (S2005). The energy impartation distribution is thereby calculated, and the measurement comes to en end (S2006).

Figure 15A:
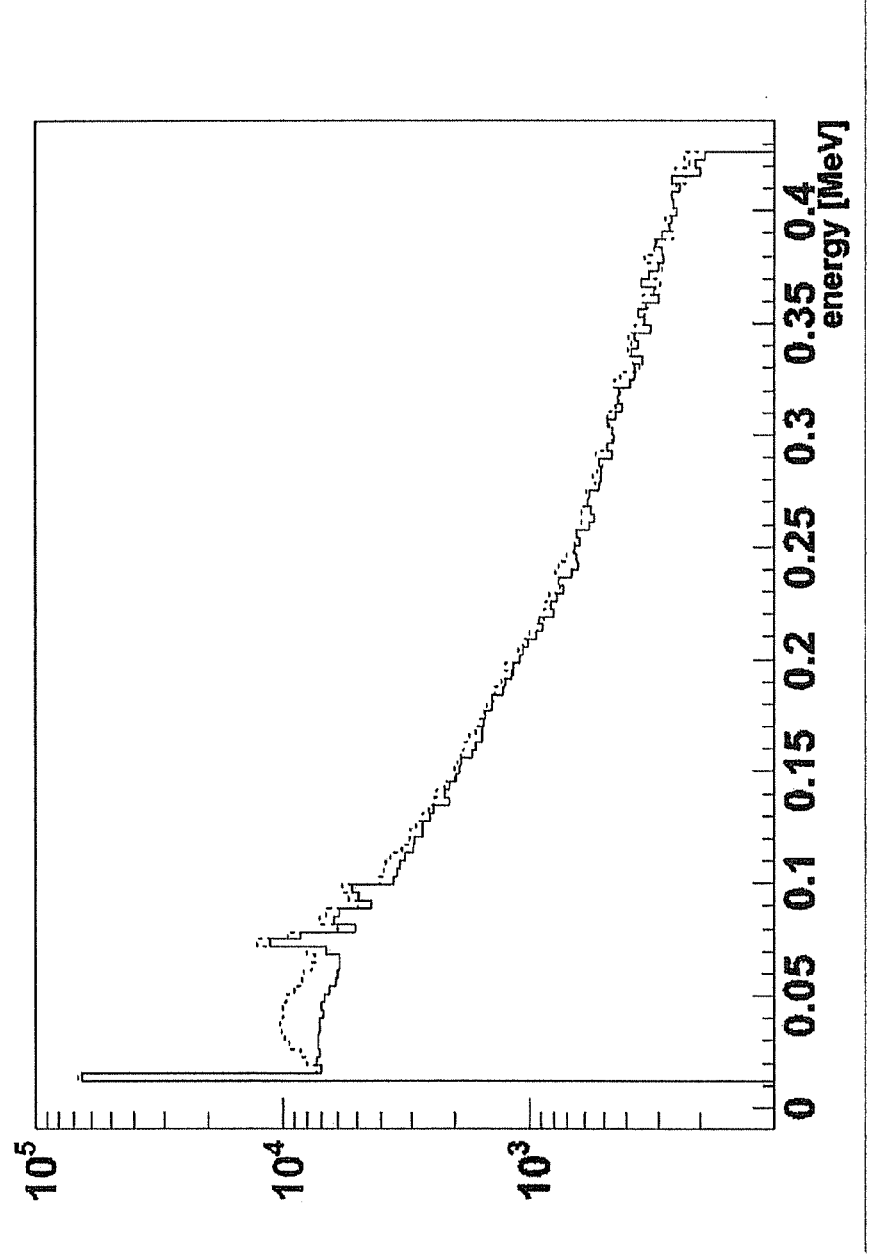
FIG. 15A is a diagram illustrating a result of measuring the energy spectrums of X-rays and gamma rays containing the braking radiations in the third embodiment.
Figure 15B:
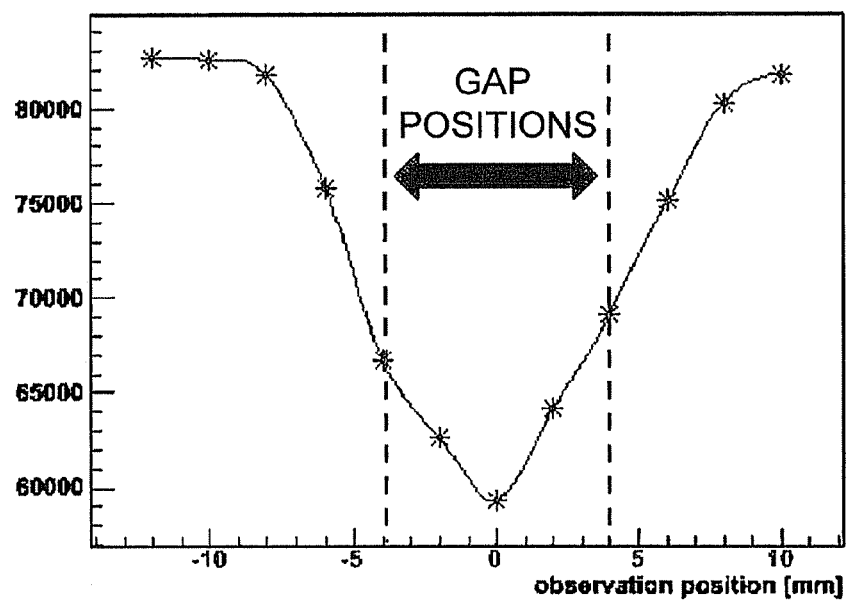
FIG. 15B is a diagram illustrating the energy impartation distribution obtained in the operational example in the third embodiment.

Note that FIG. 15A depicts an example of the energy spectrums of the braking radiations in detecting positions of 0 mm and −12 mm, which are detected by the detecting unit 11 in S2001. Further, FIG. 15B illustrates an example of the energy impartation distribution calculated by the calculating unit 31 in S2005. The detection result with the high accuracy could not be acquired due to a factor that the width of the lead collimator 120 was comparatively large and a factor that the single cadmium telluride semiconductor detector having the width of 5 mm was used as the detector 111.

It is, however, understood from FIG. 15B that the energy impartation proportional to the intensity of the braking radiation decreases in the gap position. That is, there is obtained the energy impartation distribution with the smaller braking radiation in the gap (air) portion than in the acryl portion. This demonstrates that the energy impartation distribution can be calculated by the technique according to the third embodiment.

<Others>

A description of an example of a particle radiation therapeutic method using the energy impartation distribution measuring technique of the third embodiment will be made by way of a supplement.

An operator (technician) makes a plan as a therapeutic plan for a beam path for thoroughly treating the affected part with less influence on normal healthy parts, the beam energy, an amount of ion irradiation, etc before the medical treatment. For this plan, at first, the technician consolidates compositions of the matters of the parts (areas) through which the beams used for the treatment pass in a I body of the patient. Then, the technician calculates the energy impartation at every point on the path by referring to the data table. Note that simultaneously with this calculation, the ion energy at every point on the path is also calculated. Through this calculation, the technician obtains the energy impartation distribution assumed in the therapeutic plan.

Then, the technician irradiates the ion beams according to the therapeutic plan when performing the actual treatment. At this time, the energy impartation distribution described in <Operational Example> undergoes monitoring. With this monitoring, the technician compares the energy impartation distribution assumed in the therapeutic plan with the energy impartation distribution obtained from the actual measurement. If the energy impartation distribution obtained from the actual measurement is different from the energy impartation distribution assumed in the therapeutic plan, such a case is assumed that an effect of the particle therapy is not acquired depending on a degree of this difference. For instance, if the effect of the particle therapy is not acquired, the technician makes again the plan for the beam path, the beam energy, the amount of ion irradiation, etc by employing the distribution of the internal matter density serving as a basis on which the energy impartation distribution is calculated through the actual measurement. Then, the technician recalculates the energy impartation distribution by use of the respective re-planned conditions, and updates attribute values of the ion beams used for the radiotherapy.

The technician is thereby enabled to monitor in real time the behaviors of the irradiation ion beams within the body. Then, the technician can irradiate the ion beams effective in the treatment by employing the information (behaviors) monitored in real time.

Fourth Embodiment

Finally, a fourth embodiment will be discussed. The fourth embodiment involves measuring the energy impartation distribution of the SOBP beams.

<Derivation and Example of Configuration of Apparatus>

As discussed in the second embodiment, the SOBP beams have the ion energy that continuously spread, and therefore the braking radiation also becomes what is superposed with the ion energy. Then, as the ion energy of the incident particles gets higher, the maximum energy of the braking radiation rises, and the intensity of the braking radiation also augments. Accordingly, the energy spectral distribution of the braking radiation undergoes the dominant influence due to the ions having the maximum energy in the incident particle. Namely, the braking radiation emitted when the SOBP beams enter is substantially the same as in the case of getting the monochrome beams incident, and therefore the energy impartation distribution can be obtained by absolutely the same method as in the third embodiment.

Operation and Effect of Embodiment

Each of the particle radiation monitoring apparatuses according to the first through fourth embodiments discussed so far calculates the arrival depth of the particle beams or the energy impartation distribution of the monochrome beams or the SOBP beams by using the braking radiation that has not hitherto been utilized as the background. Namely, the particle radiation monitoring apparatus according to the present embodiment estimates the radiation dose by employing the braking radiation.

The braking radiation is of promptness (prompt radiation), and hence the particle radiation monitoring apparatus according to the present embodiment can avoid a harmful influence trouble due to a washout effect. Further, unlike the measurement of the gamma rays generated by the nuclear reaction based on the conventional technique, the present embodiment utilizes the braking radiation beams of which the occurrence count is approximately $10^2$-fold to $10^5$-fold as large as others, and therefore even the small quantity of irradiation ions enable the energy impartation distribution to be measured.

That is, according to the present embodiment, the real-time monitoring, which has hitherto been difficult to attain, can be performed.

In the heavy particle radiotherapy for cancer defined as the forefront therapy, the number of irradiation ions is about one tenth as small as the proton beams. The decrease in the number of irradiation ions, leads to a reduction in the occurrence count of the gamma rays, and consequently it is further difficult to obtain sufficient statistics for presuming the energy impartation distribution. By contrast, the occurrence probability of the braking radiation beams used by the technique according to the present embodiment rises as the ion valence increases, and hence this technique is suited to the heavy particle beams as well.

Moreover, as compared with the monitoring technique, i.e., the conventional technique, using the positron emission nuclides, there is no necessity for utilizing the large scale of apparatus as in the case of the PET, the small-size and low-cost apparatus such as the cadmium telluride semiconductor detector exemplified in the present embodiment may be sufficient and is therefore excellent in terms of cost performance.

The present embodiment can provide the technique of monitoring in real time the energy impartation distribution of the particle beams in the field of the particle radiotherapy of which the utilization spreads worldwide.

The present embodiment aims at providing the particle radiation monitoring apparatus, the particle radiation monitoring program and the particle radiation monitoring method each enabling the information on the behaviors of the particle beams to be monitored in real time. Then, according to the present embodiment, it is feasible to provide the particle radiation monitoring apparatus, the particle radiation monitoring program and the particle radiation monitoring method each enabling the information on the behaviors of the particle beams to be monitored in real time.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A particle radiation monitoring apparatus comprising:
   a detecting unit to detect radioactive ray information of braking radiation from electrons undergoing action of particle beams incident on an irradiation body in accordance with a positional relation with the irradiation body; and
   a calculating unit to calculate information on behaviors of the particle beams in the irradiation body from the radioactive ray information of the braking radiation corresponding to the positional relation that is detected by said detecting unit.

2. The particle radiation monitoring apparatus according to claim 1, wherein the information on the behaviors of the particle beams is an arrival depth of the particle beams.

3. The particle radiation monitoring apparatus according to claim 1, wherein the information on the behaviors of the particle beams is an energy impartation distribution of the particle beams.

4. The particle radiation monitoring apparatus according to claim 1, wherein the particle beams are monochrome beams with single incident energy or Spread-Out Bragg Peak beams.

5. The particle radiation monitoring apparatus according to claim 2, wherein the particle beams are monochrome beams with single incident energy or Spread-Out Bragg Peak beams.

6. The particle radiation monitoring apparatus according to claim 3, wherein the particle beams are monochrome beams with single incident energy or Spread-Out Bragg Peak beams.

7. A non-transitory recording medium to retain a particle radiation monitoring program for causing a computer to:
   detect radioactive ray information of braking radiation from electrons undergoing action of particle beams incident on an irradiation body in accordance with a positional relation with the irradiation body; and
   calculate information on behaviors of the particle beams in the irradiation body from the radioactive ray information of the braking radiation corresponding to the positional relation that is detected in said detecting step.

8. A particle radiation monitoring method that causes a computer to:
   detect radioactive ray information of braking radiation from electrons undergoing action of particle beams incident on an irradiation body in accordance with a positional relation with the irradiation body; and
   calculate information on behaviors of the particle beams in the irradiation body from the radioactive ray information of the braking radiation corresponding to the positional relation that is detected in said detecting step.

\* \* \* \* \*